US009211339B2

(12) United States Patent
Cunningham

(10) Patent No.: US 9,211,339 B2
(45) Date of Patent: Dec. 15, 2015

(54) COMPOSITIONS FOR DELIVERY OF CARGO SUCH AS DRUGS PROTEINS AND/OR GENETIC MATERIALS

(71) Applicant: Terapio Corporation, Austin, TX (US)

(72) Inventor: Casey C. Cunningham, Whitehouse, TX (US)

(73) Assignee: TERAPIO CORPORATION, Austin, TX (US)

( * ) Notice: Subject to any disclaimer, the term of this patent is extended or adjusted under 35 U.S.C. 154(b) by 0 days.

(21) Appl. No.: 14/230,986

(22) Filed: Mar. 31, 2014

(65) Prior Publication Data

US 2014/0294929 A1 Oct. 2, 2014

Related U.S. Application Data

(63) Continuation of application No. 12/866,439, filed as application No. PCT/US2009/033583 on Feb. 9, 2009, now abandoned.

(60) Provisional application No. 61/026,964, filed on Feb. 7, 2008.

(51) Int. Cl.
| | |
|---|---|
| *A61K 9/127* | (2006.01) |
| *A61K 9/16* | (2006.01) |
| *C12N 15/11* | (2006.01) |
| *A61K 47/42* | (2006.01) |
| *A61K 48/00* | (2006.01) |
| *A61K 31/713* | (2006.01) |
| *C12N 15/113* | (2010.01) |
| *A61K 38/00* | (2006.01) |

(52) U.S. Cl.
CPC ............. *A61K 47/42* (2013.01); *A61K 9/127* (2013.01); *A61K 9/1271* (2013.01); *A61K 31/713* (2013.01); *A61K 48/0008* (2013.01); *C12N 15/113* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,120,198 | A | 9/2000 | Sawano et al. |
| 6,750,015 | B2 | 6/2004 | Horwitz et al. |
| 7,611,839 | B2 | 11/2009 | Twine et al. |
| 8,163,692 | B2 | 4/2012 | Awasthi et al. |
| 8,486,410 | B2 | 7/2013 | Awasthi et al. |
| 8,586,553 | B2 | 11/2013 | Awasthi et al. |
| 2002/0119156 | A1 | 8/2002 | Chen et al. |
| 2003/0138793 | A1 | 7/2003 | Su et al. |
| 2004/0156853 | A1 | 8/2004 | Awasthi et al. |
| 2005/0123594 | A1 | 6/2005 | Awasthi et al. |
| 2005/0208054 | A1 | 9/2005 | Czech et al. |
| 2006/0030536 | A1* | 2/2006 | Yu et al. ............ 514/44 |
| 2006/0182749 | A1 | 8/2006 | Awasthi et al. |
| 2008/0279919 | A1 | 11/2008 | Awasthi et al. |
| 2011/0020432 | A1 | 1/2011 | Cunningham |
| 2011/0020433 | A1 | 1/2011 | Cunningham |

FOREIGN PATENT DOCUMENTS

| | | |
|---|---|---|
| JP | 2013/500264 | 1/2013 |
| WO | 2007/102735 A1 | 9/2007 |
| WO | 2007/127439 | 11/2007 |

OTHER PUBLICATIONS

Wang et al., Biodrugs, 2009; 23(1)15-23.*
Office Action issued Jul. 3, 2014, in Israeli Application No. 217535, English translation.
Office Action issued Jul. 15, 2014, in Chinese Application No. 200980111647.9, with English translation.
Office Action issued Aug. 14, 2014, in U.S. Appl. No. 14/055,739.
Johnstone et al., Immunochemistry in Practice, 2nd Ed., Blackwell Scientific Publications, 1987, pp. 49-50.
Office Action issued Feb. 9, 2015, in Chinese Application No. 201080042245.0, with English Translation.
Office Action issued Mar. 24, 2015, in U.S. Appl. No. 13/912,631.
"American Type Culture Collection", Tumor Cell lines, 2001, pp. 1-12.
Princeton.edu, "Biological Effects of Ionizing Radiation", Open Source Radiation Safety Training. Module 3: Biological Effects.
U.S. NRC Fact Sheet "Biological Effects of Radiation", Dec. 2004, pp. 1-9.
Awasthi et al., "A Novel Mechanism of Drug Resistance in Epilepsy", Blood Brain Barrier Conference at Cleveland Clinic Foundation, Cleveland, OH, Nov. 2-3, 2004, (Abstract).
Awasthi et al., "Anti-RLIP76 Antibodies Induce Apoptosis and Enhance Doxorubicin Cytotoxicity in Lung Cancer Cells", American Association for Cancer Research, 92nd Annual Meeting, New Orleans, LA, Proceedings: 42, Mar. 24-28, 2001, (Abstract 1507).
Awasthi et al., "Anti-RLIP76 Antibodies Induce Apoptosis in Lung Cancer Cells and Display Marked Synergy with Doxorubicin", American Association for Cancer Research, 93rd Annual Meeting, San Francisco, CA; Proceedings: 43, Apr. 6-10, 2002, (Abstract 4717).
Awasthi et al., "ATP-Dependent Colchicine Transport by Human Erythrocyte Glutathione Conjugate Transporter", Toxicology and Applied Pharmacology, vol. 155, Issue 3, 1999, pp. 215-226.
Awasthi et al., "ATP-Dependent Human Erythrocyte Glutathione-Conjugate Transporter. I. Purification, Photoaffinity Labeling, and Kinetic Characteristics of ATPase Activity", Biochemistry, vol. 37, Issue 15, 1998, pp. 5231-5238.
Awasthi et al., "ATP-Dependent Human Erythrocyte Glutathione-Conjugate Transporter. II. Functional Reconstitution of Transport Activity", Biochemistry, vol. 37, Issue 15, 1998, pp. 5239-5248.

(Continued)

*Primary Examiner* — Doug Schultz
(74) *Attorney, Agent, or Firm* — Kilpatrick Townsend & Stockton LLP

(57) ABSTRACT

Compositions and methods for delivery of cargo molecules to a patient or subject in need thereof include a proteoliposome carrier vehicle that incorporates an RLIP76 protein and contains the cargo molecule. The vehicle effectively delivers the cargo molecule systemically throughout the tissues of the body including into the central nervous system.

13 Claims, 9 Drawing Sheets

(56) References Cited

OTHER PUBLICATIONS

Awasthi, "Functional Reassembly of ATP-Dependent Xenobiotic Transport by The N- and C-Terminal Domains of RLIP76 and Identification of ATP Binding Sequences", Biochemistry, vol. 40, Issue 13, 2001, pp. 4159-4168.
Awasthi, "Novel Function of Human RLIP76: ATP-Dependent Transport of Glutathione Conjugates and Doxorubicin", Biochemistry, vol. 39, Issue 31, 2000, pp. 9327-9334.
Awasthi et al., "RALPB1 is a major determinant of radiation sensitivity and glutathione-Conjugate transport", American Association for Cancer Research, 95th Annual Meeting, Orlando, FL, Mar. 27-31, 2004, (Abstract).
Awasthi et al., "RLIP76 and Cancer", Clinical Cancer Research, vol. 14, No. 14, 2008, pp. 4372-4377.
Awasthi et al., "RLIP76 Mediates Doxorubicin Transport and Resistance in Lung Cancer", 18th Annual Meeting of the International Society for Biological Therapy of Cancer (ISBTCI) Bethesda, MD, Oct. 30-Nov. 2, 2003, (Abstract).
Awasthi et al., "RLIP76, a non-ABC transporter, and drug resistance in epilepsy", BMC Neuroscience, vol. 6, 2005, pp. 61-71.
Awasthi et al., "RLIP76, a Novel Transporter Catalyzing ATP-Dependent Efflux of Xenobiotics", Drug Metabolism and Disposition, vol. 30, Issue 12, 2002, pp. 1300-1310.
Awasthi et al., "RLIP76 Is a Major Determinant of Radiation Sensitivity", Cancer Res., vol. 65, No. 14, 2005, pp. 6022-6028.
Awasthi et al., "Role of RLIP76 in lung cancer doxorubicin resistance: II. Doxorubicin transport in lung cancer by RLIP76", International Journal of Oncology, vol. 22, No. 4, 2003, pp. 713-720.
Awasthi et al., "Role of RLIP76 in lung cancer doxorubicin resistance: III. Anti-RLIP76 antibodies trigger apoptosis in lung cancer cells and synergistically increase doxorubicin cytotoxicity", International Journal of Oncology, vol. 22, No. 4, 2003, pp. 721-732.
Awasthi et al., "Targeting Multiple Signaling Pathways with RLIP76, Gordon Conference on Molecular Therapeutics of Cancer", Colby Sawyer College, New London New Hampshire, Jul. 20, 2005, (Abstract).
Awasthi et al., "Transport of glutathione conjugates and chemotherapeutic drugs by RLIP76 (RALBP1): A novel link between G-protein and tyrosine kinase signaling and drug resistance", International Journal of Cancer, vol. 106, Issue 5, 2003, pp. 635-646.
Awasthi et al., "Tyrphostin and Genistein Inhibit ATPase and transport activity of RLIP76 and increase doxorubicin toxicity in lung cancer cells", American Association of Cancer Research, 94th Annual Meeting, Washington, D.C., Jul. 11-14, 2003, (Abstract).
Baglia et al., "A Binding Site for Thrombin in the Apple 1 Domain of Factor XI", The Journal of Biological Chemistry, vol. 271, No. 7, 1996, pp. 3652-3658.
Black et al., "Effects of Dietary Constituents on Ultraviolet Light-mediated Carcinogenesis", Cancer Research, vol. 38, No. 5, May 1978, pp. 1384-1387.
Cheng et al., "Accelerated Metabolism and Exclusion of 4-Hydroxynonenal through Induction of RLIP76 and hGST5.8 Is an Early Adaptive Response of Cells to Heat and Oxidative Stress", The Journal of Biological Chemistry, vol. 276, No. 44, 2001, pp. 41213-41223.
Dainiak, "Hematologic consequences of exposure to ionizing radiation", Experimental Hematology, vol. 30, No. 6, 2002, pp. 513-528.
Dermer et al., "Another Anniversary for the War on Cancer", Biotechnology vol. 12, No. 3, 1994.
Devi, "siRNA-based approaches in cancer therapy", Cancer Gene Therapy, vol. 13, No. 9, 2006, pp. 819-829.
Drake, "RALBP1 in Stress Resistance", The University of Texas at Arlington, Thesis, Dec. 2007, pp. 1-120.
Felnerova et al., "Liposomes and Virosomes as Delivery Systems for Antigens, Nucleic Acids and Drugs", Current Opinion in Biotechnology, vol. 15, 2004, pp. 518-529.
Freshney, "Culture of Animal Cells", A Manual of Basic Technique, 1983, pp. 3-4.
Hanly et al., "Review of Polyclonal Antibody Production Procedures in Mammals and Poultry," ILAR Journal, 1995, vol. 37, No. 3, pp. 93-115.
Iyer et al., "Effects of ionizing radiation in targeted and nontargeted cells", Archives of Biochemistry and Biophysics, vol. 376, No. 1, 2000, pp. 14-25.
Kumar et al., "Gene manipulation through the use of small interfering RNA (siRNA): from in vitro to in vivo applications", Advanced Drug Delivery Reviews, vol. 59 (2-3), 2007, pp. 87-100.
Leenaars et al., "The Production of Polyclonal Antibodies in Laboratory Animals", ATLA, vol. 27, 1999, pp. 79-102.
Li et al., Chinese Pharmaceutical Journal, vol. 40, No. 19, 2005, pp. 1444-1448.
Margutti et al., "Autoantibodies to the C-terminal subunit of RLIP76 induce oxidative stress and endothelial cell apoptosis in immune-mediated vascular diseases and atherosclerosis", Blood, vol. 111, No. 9, Nov. 2007, pp. 4559-4570.
Merriam-Webster online dictionary "prevent," pp. 1-3, printed Dec. 17, 2013.
"Ultraviolet Radiation Guide," Navy Environmental Health Center, Apr. 1992, 21 pages.
Ponnappa et al., "In vivo delivery of antisense oligonucleotides in pH-sensitive liposomes inhibits lipopolysaccharide-induced production of tumor necrosis factor-$\alpha$ in rats", Journal of Pharmacology and Experimental Therapeutics, vol. 297, 2001, pp. 1129-1136.
Rutgers "Factsheet," Environmental Sciences Training Center, 1996, section 3; 3 pages.
Sause, "The Role of Radiotherapy in Non-Small Cell Lung Cancer", Chest, vol. 116 (Supplement), Issue 3, 1999, pp. 504S-508S.
Sharma et al., "RLIP76 (RALBP1)-mediated transport of leukotriene C4 (LTC4) in cancer cells: Implications in drug resistance", International Journal of Cancer, vol. 112, Issue 6, 2004, pp. 934-942.
Sharma et al., "RLIP76 is the Major ATP-Dependent Transporter of Glutathione- Conjugates and Doxorubicin in Human Erythrocytes", Archives of Biochemistry and Biophysics, vol. 391, Issue 2, 2001, pp. 171-179.
Singhal et al., "Regression of melanoma in a murine model by RLIP76 depletion," Cancer Research, vol. 66, No. 4, 2006, pp. 2354-2360.
Singhal et al., "Depletion of RLIP76 sensitizes lung cancer cells to doxorubicin", Biochemical Pharmacology, vol. 70, No. 3, 2005, pp. 481-488.
Singhal et al., "Purification and functional reconstitution of intact ral-binding GTPase activating protein, RLIP76, in artificial liposomes", ACTA Biochimica Polonica, vol. 48, No. 2, 2001, pp. 551-562.
Singhal et al., "Regression of lung and colon cancer xenografts by depleting or inhibiting RLIP76 (Ral-binding protein 1)", Cancer Research, vol. 67, 2007, pp. 4382-4389.
Singhal, "Regression of prostate cancer xenografts by RLIP76 depletion", Biochem. Pharmacal., vol. 77, No. 6, 2009, pp. 1074-1083.
Singhal et al., "RLIP76 in defense of radiation poisoning", International Journal of Radiation Oncology Biology Physics, vol. 72, No. 2, 2008, pp. 553-561.
Singhal et al., "Role of RLIP76 in lung cancer doxorubicin resistance: I. The ATPase activity of RLIP76 correlates with doxorubicin and 4-hydroxynonenal resistance in lung cancer cells", International Journal of Oncology, vol. 22, No. 2, 2003, pp. 365-375.
Singhal et al., "The role of PKC$\alpha$ and RLIP76 in transport-mediated doxorubicin-resistance in lung cancer", FEBS Letters, vol. 579, No. 30, 2005, pp. 4635-4641.
Sioud et al., "Cationic liposome-mediated delivery of siRNAs in adult mice", Biochemical and Biophysical Research Communications, vol. 312, No. 4, 2003, pp. 1220-1225.
Soranzo et al., "Lack of Support for a Role of RLIP76 (RALBP1) in Response to Treatment or Predisposition to Epilepsy", Epilepsia, vol. 48, No. 4, 2007, pp. 674-683.
Stuckler et al., "RLIP76 Transports Vinorelbine and Mediates Drug Resistance in Non-Small Cell Lung Cancer", Cancer Research, vol. 65, No. 31, 2005, pp. 991-998.

(56) References Cited

OTHER PUBLICATIONS

"Natural and Man-Made Radiation Sources," Reactor Concepts Manual, USNRC Technical Training Center, Feb. 2001, pp. 6-1 to 6-12.
Wagner, "Treatment of radiation exposure and contamination", Radiographies vol. 14, No. 2, 1994, pp. 387-396.
Weiner, "An Overview of Monoclonal Antibody Therapy of Cancer", Seminars in Oncology, vol. 26, No. 4, Suppl. 12, 1999, pp. 41-50.
Wickramarachchi et al., "Identification of Membrane Anchoring Domains of RLIP76 Using Deletion Mutant Analysis", American Association of Cancer Research, 96th Annual Meeting Anaheim, CA, Apr. 16-20, 2005, (Abstract).
Yadav et al., "Identification of Membrane-Anchoring Domains of RLIP76 Using Deletion Mutant Analyses", Biochemistry, vol. 43, 2004, pp. 16243-16253.
Yadav et al., "POB1 over-expression inhibits RLIP76-mediated transport of glutathione-conjugates, drugs and promotes apoptosis", Biochemical and Biophysical Research Communications, vol. 328, 2005, pp. 1003-1009.
Yang et al., "Role of Glutathione S-Transferases in Protection against Lipid Peroxidation: Overexpression of hGSTA2-2 in K562 Cells Protects Against Hydrogen Peroxide-Induced Apoptosis and Inhibits JNK and Caspase 3 Activation", Journal of Biological Chemistry, vol. 276, No. 22, 2001, pp. 19220-19230.
Office Action issued Jan. 17, 2014, in U.S. Appl. No. 13/912,631.
Office Action issued Jan. 9, 2014, in U.S. Appl. No. 13/912,788.
Office Action issued Mar. 7, 2014, in Chinese Application No. 201080042245.0.
Office Action issued Mar. 11, 2014, in European Application No. 10802970.3.
Office Action issued Mar. 19, 2014, in Israeli Application No. 207248.
Office Action issued May 7, 2014, in European Application No. 0907279.7.
Office Action issued Jun. 4, 2014, in U.S. Appl. No. 13/912,788.
Office Action issued May 28, 2014, in Eurasian Application No. 201270192.
Office Action issued Jun. 20, 2014, in U.S. Appl. No. 14/055,739.
Office Action issued Jul. 7, 2014, in U.S. Appl. No. 13/912,631.
Office Action issued Aug. 25, 2014, in Japanese Application No. 2012-521840, with English Translation.
Office Action issued Aug. 18, 2014, in Chinese Application No. 201080042245.0, with English Translation.
Office Action issued Sep. 5, 2014, in U.S. Appl. No. 12/842,705.
Office Action issued Nov. 11, 2014, in Eurasian Application No. 201270192, with English translation.
Office Action issued Nov. 26, 2014, in Australian Application No. 2009212143.
Examination Report issued Oct. 17, 2014, in Australian Application No. 2010275468.
Examination Report issued Aug. 20, 2015, in Australian Application No. 2010275468, 3 pages.
Office Action issued Aug. 26, 2015, in U.S. Appl. No. 14/312,523, 14 pages.
Office Action issued Aug. 14, 2015, in Chinese Application No. 200980111647.9, with English translation, 13 pages.
Office Action issued Sep. 7, 2015, in Japanese Application No. 2012-521840, with English translation, 9 pages.
Office Action issued Apr. 29, 2015, in U.S. Appl. No. 12/842,705.
Ali et al., "Role of Anserine and/or Zinc in Modulating Nucleic Acid and Protein Disorders in rats Exposed to Gamma Irradiation," Journal of Pharmacology and Toxicology, 2007, vol. 2, No. 1, pp. 1-19.
Office Action issued May 11, 2015, in Israel Application No. 217535 (English Translation Only).
Office Action issued May 20, 2015, in Eurasian Application No. 201270192, with English Translation.
Office Action issued Jun. 4, 2015, in Israel Application No. 207248 (English Translation Only).
Office Action issued Aug. 5, 2015, in U.S. Appl. No. 13/912,631.
Mani et al., "Demonstrations of Equilibrative Nucleoside Transporters (hENT1 and hENT2) in Nuclear Envelopes of Cultured Human Choriocarcinoma (BeWo) Cells by Functional Reconstitution in Proteoliposomes," Journal of Biological Chemistry, 1998, vol. 273, No. 46, pp. 30818-30825.
Hammond et al., "Functional Reconstitution of Pharmacologically Distinct Subtypes of Nucleoside Transporters in Liposomal Membranes," Journal of Pharmacology and Experimental Therapeutics, 1994, vol. 271, No. 2, pp. 906-917.
Office Action issued Aug. 11, 2015, in U.S. Appl. No. 14/622,738, 10 pages.

\* cited by examiner

COMPOSITIONS FOR DELIVERY OF CARGO SUCH AS DRUGS PROTEINS AND/OR GENETIC MATERIALS

CROSS-REFERENCE TO RELATED APPLICATIONS

This application is a continuation application of U.S. Ser. No. 12/866,439, filed Oct. 8, 2010, abandoned, which is a National Stage application of International Application No. PCT/US2009/033583, filed Feb. 9, 2009, which claims the benefit of U.S. Application Ser. No. 61/026,964 filed Feb. 7, 2008. The disclosure of each of these applications is incorporated by reference herein in its entirety.

BACKGROUND OF THE INVENTION

Liposomes have been commonly tried for the delivery of genetic material (reviewed in Simoes, et al., *Expert Opin. Drug Deliv.* 2:237-254, 2005). However, they suffer from several drawbacks, including binding by serum components (Pedroso de Lima, et al., *Curr. Med. Chem.* 10:1221-1231, 2003), preferential absorption in endothelial cells of blood vessels (Dass and Choong, *J. Control Release* 113:155-163, 2006), and poor delivery systemically. Targeting moieties have allowed specific delivery to lung (Kawakami, et al., *Crit. Rev. Ther. Drug Carrier Syst.* 19:171-190, 2002) and liver (Kawakami, et al., *Pharm. Res.* 17:306-313, 2000).

The delivery of biologically active proteins using liposomes has remained more of a laboratory exercise (Sells, et al., *Biotechniques* 19:72-76, 78, 1995), and other methods such as virosomes have shown some superiority (Bungener, et al., *Biosci. Rep.* 22:323-338, 2002). Therefore, this represents an area where new methods and compositions are clearly needed.

In addition, many tissues are considered difficult to access via systemic liposomal delivery systems, including the brain, so direct injection techniques have had to be employed instead (Huynh, et al., *J. Control Release* 110:236-259, 2006). As local injection limits the amount of tissue that can be reached, there is a clear need for systemic delivery to the central nervous system.

SUMMARY OF THE INVENTION

The present disclosure demonstrates the remarkable ability of RLIP76 proteoliposomes to deliver cargo molecules in the body while retaining functionality of the delivered cargos. The RLIP76 proteoliposomes are able to deliver their cargos systemically, and to specific tissues, including, but not limited to, the central nervous system, lung, liver, heart, and kidney tissues. The cargo molecules that may be delivered by the RLIP76 proteoliposomes include nucleic acid molecules, RNA molecules, DNA molecules, small interfering RNA (siRNA) molecules, antisense molecules, polynucleotide molecules, oligonucleotide molecules; protein molecules, and other small molecules. A RLIP76 proteoliposome may contain one or more cargo molecules. In certain embodiments, the RLIP proteoliposomes having one or more cargo molecules is administered orally for in vivo delivery of the cargo molecules. In other embodiments, the RLIP proteoliposomes having one or more cargo molecules is delivered in a pharmaceutically acceptable carrier.

One aspect of the present disclosure is directed to RNA interference compositions ("RNAi compositions"). These compositions comprise a RLIP76 proteoliposome comprising an RNAi molecule, for example a small interfering RNA ("siRNA"). The RLIP76 proteoliposome facilitates transfer of a functional RNAi molecule into a cell, in vitro or in vivo. In certain embodiments, the RNAi compositions of the present disclosure are administered for the purposes of inhibiting expression of a selected target gene, mRNA, or protein in the cell.

The present disclosure provides methods of delivering a cargo molecule to a cell, comprising contacting the cell with a proteoliposome comprising an RLIP76 protein and at least a first cargo molecule. In certain embodiments, the cell is a brain, heart, liver, kidney, lung, or eye cell. In particular embodiments, the cell is a neuron, for example a dopaminergic, GABAergic, serotonergic, or glutamatergic neuron, or a glial cell, for example an astrocyte or an oligodendrocyte. In other embodiments, the cell is a tumor cell. In further embodiments, the cell is a human cell. In still further embodiments, the cell is an endothelial cell, for example an endothelial cell of a blood vessel, or an endothelial cell of a blood vessel in the brain.

The present disclosure also provides compositions comprising a proteoliposome comprising an RLIP76 protein and a cargo molecule, wherein the proteoliposome is in a pharmaceutically acceptable carrier. In certain embodiments, the pharmaceutically acceptable carrier is formulated for oral, intraperitoneal, intravenous, intramuscular, inhalation, transmucosal, transdermal, respiratory, pulmonary, or nasal administration.

Additionally, the present disclosure provides methods of delivering a cargo molecule to a subject in need thereof comprising administering to the subject a therapeutically effective amount of a pharmaceutical composition comprising a proteoliposome in a pharmaceutically acceptable carrier, wherein the proteoliposome comprises an RLIP76 protein and the cargo molecule.

In certain aspects, the cargo molecule is a nucleic acid molecule or a polypeptide molecule. In particular aspects, the cargo molecule is a DNA molecule, an RNA molecule, an antisense RNA molecule, a RNA inhibitory molecule, a small or short inhibitory RNA molecule, a ribozyme molecule, a triplex molecule, an aptomer molecule, a short hairpin RNA molecule, a microRNA molecule, a tiny non-coding RNA molecule, or a small modulatory RNA molecule. In other aspects, the cargo molecule is a nucleic acid molecule that is operably linked to a tissue-specific promoter or a cell-specific transcriptional response element.

In certain embodiments, the proteoliposome comprises RLIP76 and a plurality of cargo molecules. In other embodiments, the proteoliposome further comprises at least a first therapeutic agent. In further embodiments, the proteoliposome further comprises a targeting moiety, for example a cell-specific or tissue-specific targeting moiety. In particular embodiments, the targeting moiety is an antibody, a monoclonal antibody, an antibody fragment, or a single chain antibody, a protein or protein fragment, a hormone, or a chemical moiety.

In further aspects, the RLIP76 protein is a human RLIP76 protein. In other aspects, the RLIP76 protein is one or more fragments of the human RLIP76 protein that alone or in combination retain RLIP76 transport activity. In particular aspects, the RLIP76 protein is a combination of the human N-RLIP76$_{1-367}$ and human C-RLIP76$_{410-655}$ polypeptide fragments. In yet other aspects, the RLIP76 protein is a mutant RLIP76 protein that retains RLIP76 transport activity.

In certain embodiments, the cargo molecule is delivered to the brain, heart, liver, kidney, muscle, or lung of the subject. In particular embodiments, the cargo molecule is delivered to neurons or endothelial cells of blood vessels within the brain, while in other embodiments the cargo molecule is delivered to neurons and endothelial cells of blood vessels within the brain. In further embodiments, the cargo molecule is delivered to a tumor within the subject, and in yet other embodiments, the cargo molecule is delivered to a tumor within the central nervous system of the subject.

A representative embodiment of the RLIP76 proteoliposome composition disclosed herein includes an antisense oligomer to SET-1 as the cargo molecule. This cargo molecule was delivered systemically by RLIP76 proteoliposomes to several tissues tested, including brain, liver, lung, heart and kidney, and remained functional after delivery as shown by decreases in SET-1 mRNA and decreased SET-1 protein expression in several tested tissues. Surprisingly the RLIP76 proteoliposomes delivered the antisense oligomer significantly more efficiently than liposomes not containing RLIP76.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" may mean a singular object or element, or it may mean a plurality, or one or more of such objects or elements. In addition, the use of "or" means "and/or", unless specifically stated otherwise. Also, terms such as "element" or "component" encompass both elements and components comprising one unit and elements or components that comprise more than one unit unless specifically stated otherwise.

It is to be understood that both the foregoing general description and the following detailed description are exemplary and explanatory only, and are not restrictive of the invention, as claimed. The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Results of PCR using primers surrounding insertion site of RIP1 (mouse version of RLIP76). Lane M, molecular weight standards, Lane 1, PCR of homozygous RLIP76 mouse, Lane 2, PCR of heterozygous RLIP76 mouse, Lane 3, PCR of wild-type mouse. FIG. 1B. Western blot analysis of mouse liver and heart tissues using an anti-RLIP76 antibody. Lane 1, molecular weight standards, Lane 2, negative control, Lanes 3 and 6, wild-type RIP1 mice, Lanes 4 and 7, heterozygous RIP1 mice, Lanes 5 and 8, homozygous RIP1 mice.

FIG. 2A. Homozygous RIP1 knockout mice treated i.p. with RLIP76 liposomes containing 200 µg RLIP76 protein and sacrificed 48 hours later. Lanes labeled C are from mice treated with control liposomes without RLIP76, and lanes labeled R are from mice treated with RLIP76-liposomes. FIG. 2B. Homozygous RIP1 knockout mice treated with 3 doses of 200 µg RLIP76-liposomes at time 0, 72 hours, and 120 hours, followed by sacrifice at 168 hours. Lanes labeled C are from mice treated with control liposomes without RLIP76, and lanes labeled R are from mice treated with RLIP76-liposomes.

Figure 1A:
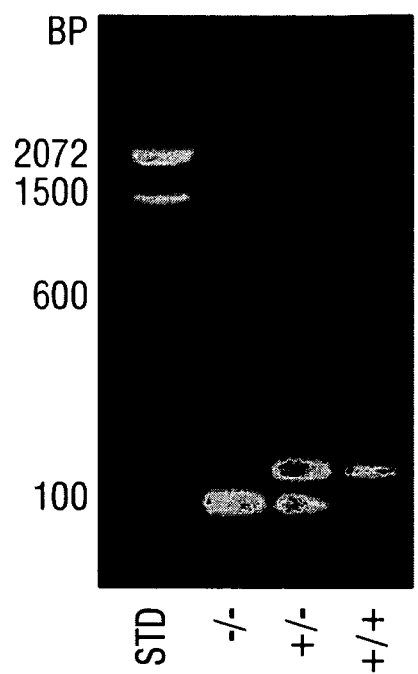
FIG. 1A and FIG. 1B.

Bands in Western blots quantified by scanning densitometry. β-actin used as internal control.

DETAILED DESCRIPTION

The present disclosure arises at least in part from the discovery that proteoliposomes containing RLIP76 protein are surprisingly effective at delivering a "cargo molecule" to various tissues of the body. As used herein, "RLIP76 proteoliposomes" refers to not only a combination of RLIP76 with liposomes, but also to combinations of RLIP76 with microemulsions, micelles, unilamellar or multilamellar vesicles, erythrocyte ghosts or spheroblasts, and the like. It is also understood that in addition to delivery of nucleic acid cargo molecules, the RLIP76 proteoliposomes are contemplated to be effective for delivery of polypeptide and small molecule cargo molecules as well (e.g., a therapeutic agent). The RLIP76 proteoliposomes disclosed herein can be used to deliver a combination of two or more nucleic acid cargo molecules; two or more polypeptide cargo molecules; two or more small molecule molecules; a nucleic acid cargo molecule and a polypeptide cargo molecule; a nucleic acid cargo molecule and a small molecule cargo molecule, a small molecule cargo molecule and a polypeptide cargo molecule, and a nucleic acid cargo molecule, a polypeptide cargo molecule, and a small molecule cargo molecule.

The preliminary animal study demonstrates the efficacy of the delivery vehicle when administered either orally or intraperitoneally, however, it is understood that delivery could also be accomplished by other ways known in the art, including, but not limited to, inhalation, intravenous, intramuscular, transmucosal or transdermal delivery. The data herein demonstrate that the disclosed delivery vehicle is effective for delivery to brain, lung, liver, heart, and kidney tissues, and it is expected that delivery is also effective for other tissues not tested in the studies shown herein. It is particularly significant that the delivery vehicle is able to deliver a cargo across the blood/brain barrier for expression in brain tissue after oral or intraperitoneal administration.

RLIP76

RLIP76 (also known as RALBP1 or RIP1) is a ubiquitous protein present from *Drosophila* to humans that serves multiple roles in cellular physiology. When membrane-associated, the protein functions as a multi-specific efflux pump for a variety of compounds, including amphiphilic small molecules such as Vinca alkaloids and anthracylines, which are common anticancer drugs. However, RLIP76 transport also involves movement from the cell of endogenous glutathione electrophile conjugates (GS-E) formed from reactive oxygen species (ROS). ROS are produced by a variety of insults such as radiation and a plethora of organic chemicals, and are toxic to the cell on many levels. As their name implies, ROS are highly reactive and bind to almost anything in their path, including proteins, lipids and nucleic acids, modifying each of these as they are contacted. The damage done to lipids (lipid peroxidation) is particularly pernicious since the peroxidation products that result are themselves toxic. These include proapoptotic reactive alkenals, such as 4-hydroxynonenal (4-HNE), which are long lived and can accumulate in the cell, ultimately leading to further damage and death. As such, RLIP76 is an important component of stress-response in cultured cells and provides protection from stressors including heat, oxidant chemicals, chemotherapeutic agents, UV irradiation and X-irradiation.

The primary structure of RLIP76 reveals several interesting features. The protein may be divided into four regions out of which two central domains carry a Rac1/CDC42 GAP activity and a Ral binding domain. The function of the two flanking domains is still unknown. The nucleotide sequence of human RLIP76 (GenBank Accession Number NM_006788) and mouse RLIP76 (NM_009067), and the amino acid sequence of human RLIP76 (GenBank Accession Number NP_006779) and mouse RLIP76 (GenBank Accession Number NP_033093) have been described. The human RLIP76 amino acid sequence includes sites for N-glycosylation (amino acids 341-344), cAMP (amino acids 113-116), cGMP-dependent protein kinase phosphorylation (amino acids 650-653), tyrosine kinase phosphorylation (amino acids 308-315), N-myristolation (amino acids 21-26, 40-45, and 191-196), leucine zipper pattern (amino acids 547-578) and several protein kinase C phosphorylation, casein kinase II phosphorylation, trypsin and chymotrypsin cut sites. The presence of such motifs in the primary structure of RLIP76, and its facile proteolytic degradation, shows RLIP76 to be involved in several intra- and extracellular processes (e.g., protein processing, intracellular signaling, protein degradation, recognition, tagging, etc.) and that proteolytic processing of RLIP76 is required for the multiple functions. The peptide fragments of RLIP76 individually or in association with other fragments may catalyze these various functions. For example, N-terminal and C-terminal fragments of RLIP76, fragments that are individually incapable of mediating ATP-dependent transport, can catalyze the transport of electrically charged drugs (e.g., DOX, colchicines) when reconstituted together in proteoliposomes.

RLIP76 expressed in cultured cells or in *E. coli* undergoes facile proteolysis during purification. Two most prominent peptides, N-RLIP76$_{1-367}$ and C-RLIP76$_{410-655}$, arising from the N- and C-termini of RLIP76, respectively, appear as 49 kDa and 38 kDa bands in SDS-gels. Both these peptides display constitutive ATPase activity that may be stimulated in the presence of the anionic or cationic ligands transported by RLIP76. Both peptides bind ATP, as shown by photoaffinity labeling that increased in the presence of vanadate, indicating the trapping of a reaction intermediate in the ATP binding site. None of the two fragments catalyze transport when reconstituted alone in proteoliposomes. However, when reconstituted together, ATP-dependent transport of charged chemicals (e.g., DNP-SG, DOX) is observed with kinetic parameters similar to those for RLIP76. The ATP binding sites in N-RLIP76$_{1-367}$ and C-RLIP76$_{410-655}$ were identified to be amino acids 69-74 and amino acids 418-425, respectively. Mutations of $K^{74}$ and $K^{425}$ in the N- and C-terminal peptides, respectively, abrogate the ATPase activity, ATP binding capacity, and transport function. The sequence of these ATP binding sites is not identical to the consensus sequence for the P-loop (Walker motif).

In addition to the human RLIP76 nucleic acid sequence described above, a number of single nucleotide polymorphisms (SNPs) have been described within the human RLIP76 gene, three of which (an A to G mutation at nucleotide 660 of the coding sequence, a G to A mutation at nucleotide 838 of the coding sequence, and a C to T mutation at nucleotide 2065 of the coding sequence) fall within the RLIP76 coding sequence, resulting in a change in the amino acid sequence from lysine to glutamate at amino acid position 149, from arginine to glutamine at amino acid position 208, and from alanine to valine at amino acid position 617, respectively. The SNPs that occur in the introns of the human RLIP76 gene, and well as the SNPs that occur in the 5' and 3'-untranslated regions of the human RLIP76 gene, are described in the Single Nucleotide Polymorphism (SNP) database on the National Center for Biotechnology Information web site.

In certain aspects of the present disclosure, "RLIP76" or "an RLIP76 protein" can refer to the full length human RLIP76 amino acid sequence as shown in GenBank Accession Number NP_006779, one or more fragments of human RLIP76 amino acid sequence that alone or in combination retain RLIP76 transport activity, or mutations of the human RLIP76 amino acid sequence that retain RLIP76 transport activity. In certain embodiments, RLIP76 can refer to an amino acid sequence that has about 99% identity or homology with the human RLIP76 amino acid sequence as shown in GenBank Accession Number NP_006779, about 98% identity or homology, about 95% identity or homology, about 90% identity or homology, about 85% identity or homology, or about 80% identity or homology to the human RLIP76 amino acid sequence as shown in GenBank Accession Number NP_006779.

Liposomes

Liposomes are vesicles consisting of amphipathic lipids arranged in one or more concentric bilayers. When lipids are placed in aqueous medium, the hydrophilic interaction of the lipid head groups with water results in the formation of multilamellar and unilamellar systems or vesicles which resemble biological membranes in the form of a spherical shell. Liposomes may be small (0.025-0.05 µm) to large multilamellar vesicles (0.05-10 µm). Lipids used to prepare the liposomes include, but are not limited to, phospholipids, sphingolipids, glycosphingolipids, saturated glycerides, steroids (e.g., cholesterol) and synthetic phospholipids. Liposomes are typically prepared by melting the lipid together in aqueous solvent with an emulsifier like polyoxyethylene (POE). The drug is then added and the liposomes are generated through mixing or sonication. The drug is usually entrapped in the vesicle structure. These basic liposomes are sometimes referred to as "conventional liposomes." Several other types of liposomal preparations exist, including, but not limited to: (1) sterically stabilized liposomes, which are surface coated with an inert hydrophilic polymer, such as polyethylene glycol; (2) targeted liposomes, to which are attached targeting ligands, such as antibodies or fragments thereof, lectins, oligosaccharides or peptides (e.g., choleratoxin B (CTB) is used to target liposomes to the gastrointestinal epithelium); and (3) reactive or "polymorphic" liposomes, which change their phase and structure in response to a particular interaction (this group includes liposomes sensitive to ions (pH, cations), heat, and light, among other stimuli).

In certain embodiments the compositions include proteoliposomes. As used herein, a "proteoliposome" is generally a protein and lectin or glyco- or phospholipid combination that forms a spherical micellular-like or vesicular structure. The structures may form spontaneously or by chemical or mechanical manipulation, or combinations thereof. Proteoliposomes take advantage of the amphipathic nature of the lipid (or lectin) that causes them to form bilayers when in solution resulting in at least one of several shapes, including: (a) spherical micelle with the tails inward; or (b) bimolecular sheets that are bilayers with hydrophobic tails sandwiched between hydrophilic head groups. In general, proteoliposomes may reseal themselves when torn or broken. Proteoliposomes may contain only one lectin or lipid, or a variety and combination of each. Examples of phospholipids include, but are not limited to, phosphatidylcholine, sphingomyelin, phosphatidylserine, inositol phospholipids, and phosphatidylethanolamine. When used, proteoliposomes may be charged or electrically neutral and are generally used at physiological pH. They may also be structures mixed with detergent (e.g., detergent/lipid/protein, detergent/lectin/protein). Methods for preparing proteoliposomes of defined lipid-protein or lectin-protein ratios and size are well-known to one of ordinary skill in the art of molecular biology and protein/lipid biochemistry.

The proteoliposomes of the disclosure can be made by any method known in the art, including, but not limited to, methods disclosed and described in United States Patent Application Publication No. US 2005/0123594 A1, the disclosure of which is incorporated herein in its entirety by reference for all purposes.

Nucleic Acid Compositions

In certain embodiments of the present disclosure, the RLIP76 liposomes or proteoliposomes are used to deliver nucleic acid molecules, including, but not limited to, RNA, DNA, antisense, polynucleotide, oligonucleotide, ribozyme, and/or triplex molecules. Such nucleic acid molecules can also encompass an RNA molecule that reduces expression of a target nucleic acid by an RNA interference (RNAi)-based mechanism. Certain exemplary RNA molecules suitable for RNAi include, but are not limited to, short interfering RNA (siRNA), short hairpin RNA (shRNA), microRNA, tiny noncoding RNA (tncRNA), and small modulatory RNA (smRNA) molecules (see, e.g., Novina and Sharp, *Nature* 430: 161-164, 2004).

The term "RNA" or "RNA molecule" or "ribonucleic acid molecule" refers to a polymer of ribonucleotides. The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively) or chemical synthesized using methods well known to those of skill in the art. RNA can be post-transcriptionally modified. DNA and RNA can be single-stranded (i.e., ssRNA and ssDNA, respectively) or multi-stranded (e.g., double stranded, i.e., dsRNA and dsDNA, respectively). The term "mRNA" or "messenger RNA" refers to single-stranded RNA that specifies the amino acid sequence of one or more polypeptide chains, which is translated during protein synthesis when ribosomes bind to the mRNA. The term "oligonucleotide" refers to a short polymer of nucleotides and/or nucleotide analogs.

As used herein, the term "small interfering RNA" or "siRNA" or "short interfering RNA" refers to an RNA (or RNA analog) comprising between about 10-50 nucleotides (or nucleotide analogs) which is capable of directing or mediating RNA interference. In certain embodiments, an siRNA comprises between about 15-30 nucleotides or nucleotide analogs, between about 16-25 nucleotides (or nucleotide analogs), between about 18-23 nucleotides (or nucleotide analogs), and between about 19-22 nucleotides (or nucleotide analogs) (e.g., 19, 20, 21 or 22 nucleotides or nucleotide analogs). In some instances an siRNA may include fewer than 19 nucleotides, e.g., 15, 16, 17 or 18 nucleotides, provided that the shorter siRNA retains the ability to mediate RNAi. Likewise, an siRNA may, in some instances, include more than 26 nucleotides, provided that the longer siRNA retains the ability to mediate RNAi absent further processing, e.g., enzymatic processing, to a shorter siRNA.

As used herein, the term "RNA interference" or "RNAi" refers to a selective intracellular degradation, for example, to modulate or silence the expression of a target gene. RNAi does not require the antisense molecule to be identical to the mRNA target sequence, but rather that the antisense molecule have a sequence sufficiently complementary to a target mRNA sequence to trigger the destruction of the target mRNA by the RNAi machinery or process (see, e.g., U.S. Pat. No. 7,459,547, which is incorporated herein in its entirety). As used herein, the terms "reduce the expression" and "silence the expression," means any reduction or silencing of expression, up to and including complete (100%) reduction and silencing of expression. In certain aspects, expression can be reduced or silenced by 5%, 10%, 15%, 20%, 25%, 30%, 35%, 40%, 45%, 50%, 60%, 70%, 75%, 80%, 90%, 95%, 96%, 97%, 98%, or 99% or more compared to expression in the absence of the reducing, interfering or silencing molecule.

In certain aspects of the present disclosure, the nucleic acid molecules comprise at least one modified base moiety that is selected from the group including, but not limited to, 5-fluorouracil, 5-chlorouracil, 5-bromouracil, 5-iodouracil, hypoxanthine, xanthine, 5-(carboxyhydroxylmethyl) uracil, dihydrouracil, 5-carboxymethylaminomethyl-2-thiouridine, 5-methylaminomethyluracil, 5-methyl-2-thiouracil, N6-adenine, 2-thiouracil, 5'-methoxycarboxymethyluracil, 5-carboxymethylaminomethyluracil, 5-methyluracil, 5-methoxyaminomethyl-2-thiouracil, 4-thiouracil, pseudouracil, uracil-5-oxyacetic acid (v), uracil-5-oxyacetic acid methylester, 3-(3-amino-3-N2-carboxypropyl) uracil, inosine, 1-methylinosine, 5-methoxyuracil, N6-isopentenyladenine, 2-methyladenine, queosine, 2-methylguanine, 2-methylthio-N6-isopentenyladenine, beta-D-galactosylqueosine, 1-methylguanine, beta-D-mannosylqueosine, 7-methylguanine, 2,2-dimethyl guanine, 3-methylcytosine, 5-methylcytosine, 4-acetylcytosine, 2-thiocytosine, wybutoxosine, (acp3)w, and 2,6-diaminopurine.

In certain embodiments of the present disclosure, the nucleic acid molecules comprise at least one modified sugar moiety selected from the group including, but not limited to, arabinose, 2-fluoroarabinose, xylulose, and hexose. In other embodiments, the nucleic acid molecules comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof. In yet other embodiments, the nucleic acid molecules are α-anomeric oligonucleotides. An α-anomeric oligonucleotide forms specific double-stranded hybrids with complementary RNA in which, contrary to the usual β-units, the strands run parallel to each other (Gautier, et al., *Nucl. Acids Res.* 15:6625-6641, 1987). The oligonucleotide can also be a 2'-O-methylribonucleotide (Inoue, et al., *Nucl. Acids Res.* 15:6131-6148, 1987), or a chimeric RNA-DNA analogue (Inoue, et al., *FEBS Lett.* 215:327-330, 1987).

The activity of an antisense nucleic acid molecule, such as an antisense DNA or siRNA molecule, is often affected by the secondary structure of the target mRNA (see, e.g., Vickers, et al., *J. Biol. Chem.* 278:7108-7118, 2003). Thus, an antisense nucleic acid can be selected that is complementary to a region of a target mRNA that is available for base pairing. A suitable region of a target mRNA can be identified by performing a "gene walk," e.g., by empirically testing a number of antisense oligonucleotides for their ability to hybridize to various regions along a target mRNA and/or to reduce target mRNA expression (see, e.g., Vickers, et al., supra, and Hill, et al., *Am. J. Respir. Cell Mol. Biol.* 21:728-737, 1999). Alternatively, a suitable region of a target mRNA can be identified using an mRNA secondary structure prediction program or related algorithm to identify regions of a target mRNA that do not hybridize to any other regions of the target mRNA (see, e.g., Hill, et al., supra). A combination of the above methods can also be used to identify a suitable region of a target mRNA.

The present disclosure is directed to certain embodiments that feature RNAi compositions, methods of making said RNAi compositions, and methods (e.g., research and/or therapeutic methods) for using the RNAi compositions. The RNAi compositions can be RLIP76 proteoliposomes comprising siRNA molecules, precursor molecules (e.g., engineered precursor molecules) that are processed into siRNA molecules, or molecules (e.g., DNA molecules) that encode, for example, precursor molecules (e.g., engineered precursor molecules).

Targets and Diseases/Disorders

The presently disclosed compositions and methods can be used to target a number of specific nucleic acid targets in a particular cell, tissue, or patient, as well as to treat a number of different diseases, disorders, and conditions.

In certain embodiments of the present disclosure, the RNAi composition comprises an antisense RNA or siRNA that is designed to target a nucleotide sequence (or in certain cases more than one nucleotide sequence) to treat or prevent neurological diseases or disorders, where it is particularly desirable that the active agent traverses the blood-brain barrier. "Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurological disease sequence targets include, but are not limited to: Alzheimer's disease targets such as mutant alleles of the β-amyloid precursor protein gene (APP), mutant alleles of the tau protein, the apolipoprotein E ε4 allele, and mutant alleles of the secretase and presenilin genes, such as β-secretase; multiple sclerosis targets such as the T-bet transcription factor, interleukin 23, and osteopontin; Parkinson's disease targets such as alpha-synuclein; and central nervous system tumor targets, such as Notch-1, cathespin B, urokinase-type plasminogen activator receptor, and matrix metalloproteinase. Additional neurological diseases and disorders that can be treated or prevented using the presently disclosed compositions and methods include, but are not limited to, hereditary spastic hemiplegia, primary lateral sclerosis, spinal muscular atrophy, Kennedy's disease, repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCAT, and SCA17), spinal and bulbar muscular atrophy (SBMA), and dentatorubropallidoluysian atrophy (DRPLA), familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy), traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoffs related dementia, neurodegenerative diseases affecting sensory neurons, including, but not limited to, Friedreich's ataxia, diabetes, peripheral neuropathy and retinal neuronal degeneration, neurodegenerative diseases of limbic and cortical systems, including, but not limited to, cerebral amyloidosis, Pick's atrophy, and Retts syndrome. In certain embodiments, the CNS condition or disorder to be treated is a brain tumor or other neoplasia (e.g., a CNS tumor such as a glioblastoma). Such tumors or neoplasia may be primary tumors or may be metastases.

In other embodiments of the present disclosure, the RNAi composition comprises an antisense RNA or siRNA that is designed to treat or prevent certain viral infections, including, but not limited to, viral infections resulting from the influenza virus, respiratory syncytial virus (RSV), pertussis virus, severe acute respiratory syndrome (SARS) virus, SARS-CoV virus, Lassa fever virus, tick-borne encephalitis virus, Dengue virus, Hepatitis B virus, Hepatitis C virus, Rabies virus, Semliki Forest virus, Ross River virus, Aura virus, Borna disease virus, Hantaan virus, and other viruses well known to those of skill in the art. RNAi is a recently discovered and developed antiviral strategy in which gene silencing is effected by siRNA, which may be delivered to a cell or subject in need thereof using the disclosed compositions and methods. For example, antiviral strategies using siRNA have been developed that are inhibitory against influenza virus (see, e.g., U.S. Pat. No. 7,304,042, and U.S. Patent Application Publication Nos. 20040242518 and 20070213293); inhibitory against RSV (see, e.g., U.S. Patent Application Publication No. 20070238676); inhibitory against human immunodeficiency virus (HIV) or lentivirus (see, e.g., U.S. Pat. No. 7,195,916); inhibitory against hepatitis virus (see, e.g., U.S. Patent Application Publication No. 20080269148); and inhibitory against SARS virus (see, e.g., U.S. Patent Application Publication No. 20050095618), each of which is incorporated herein by reference. This list is merely exemplary, and not exhaustive of antiviral strategies using siRNA that have been developed and are well known to those of skill in the art.

In yet other embodiments of the present disclosure, the RNAi composition comprises an antisense RNA or siRNA that is designed to target a nucleic acid sequence (or in certain aspects more than one nucleic acid sequence) to treat or prevent angiogenesis, for example by targeting the expression of regulatory proteins and nucleic acid molecules involved in modulating angiogenesis. The term "angiogenesis," as used herein, refers to the inappropriate formation of new blood vessels. Angiogenesis often occurs in tumors when endothelial cells secrete a group of growth factors that are mitogenic for endothelium causing the elongation and proliferation of endothelial cells, which results in a generation of new blood vessels. The inhibition of angiogenesis can cause tumor regression in animal models, suggesting a use as a therapeutic anticancer agent. An effective amount for inhibiting angiogenesis is an amount which is sufficient to diminish the number of blood vessels growing into a tumor. This amount can be assessed in an animal model of tumors and angiogenesis, many of which are known in the art. For example, siRNAs may be utilized that are specific for the vascular endothelial growth factor (VEGF) gene and the VEGF receptor genes Flt-1 and Flk-1/KDR, tumor necrosis factor α (TNFα) by silencing TNFα cell surface receptor TNF receptor-1 (TNFR1) (see, e.g., U.S. Pat. No. 7,345,027 and U.S. Patent Application Publication No. 20090036396, incorporated herein by reference). Diseases which involved angiogenesis stimulated by overexpression of VEGF, such as diabetic retinopathy, age related macular degeneration and many types of cancer, can be treated by administering the siRNAs using the disclosed compositions and methods. Additional tumorigenic sequence targets include, but are not limited to, PTEN, p53, p65, PI-3 kinase, protein kinase c-alpha, protein kinase N3, ICAM-1, H-ras, V-ras, N-ras, K-ras, raf, C-erbB2, Bcl-2, VEGF, Flt-3, and c-myc. The disclosed compositions and methods may also inhibit cancer cell growth, reduce tumor size, prevent invasiveness, inhibit cancer progression and inhibit metastasis. Thus the disclosed compositions and methods are useful for treating tumor cell proliferation or metastasis in a subject. The cancer may be a malignant or non-malignant cancer. Such cancers or tumors include, but are not limited to, biliary tract cancer; brain cancer; breast cancer; cervical cancer; choriocarcinoma; colon cancer; endometrial cancer; esophageal cancer; fibrosarcoma, gastric cancer; hepatoma, intraepithelial neoplasms; lymphomas; liver cancer; lung cancer (e.g., small cell and non-small cell); melanoma; neuroblastomas; oral cancer; ovarian cancer; pancreatic cancer; prostate cancer; rectal cancer; sarcomas; skin cancer; testicular cancer; thyroid cancer; and renal cancer, glioblastoma, as well as other carcinomas and sarcomas. Examples of other representative targets involved in modulation of angiogenesis are disclosed in U.S. Pat. No. 7,419,779, incorporated herein by reference. This list is merely exemplary, and not exhaustive of strategies to modulate angiogenesis using siRNA that have been developed and are well-known to those of skill in the art.

In certain aspects of the present disclosure, the RNAi composition comprises an antisense RNA or siRNA that is designed to target a nucleotide sequence (or in certain cases more than one nucleotide sequence) to treat or prevent a pulmonary condition, i.e., a disease or disorder that affects lung function. Pulmonary condition sequence targets include, but are not limited to, endothelial-derived FGF2 for treatment of pulmonary hypertension, and VCP/pr97 for the treatment of cystic fibrosis. Other examples of pulmonary conditions that may be treated or prevented include, but are not limited to, cystic fibrosis, asthmatic bronchitis, tuberculosis, bronchitis, bronchiectasis, laryngotracheobronchitis, bronchiolitis, emphysema, bronchial pneumonia, allergic bronchopneumonia, viral pneumonia, pertussis, diphtheria, spasmodic croup, pulmonary phthisis, encephalitis with retained secretions, pulmonary edema, cytomegaloviral pneumonia or miliary tuberculosis, drug-induced lung disease (e.g., after administration of penicillin, nitrofurantoin), neoplastic lung disease having lymphangitic spread pattern or bronchoalveolar cell carcinoma, infectious or noninfectious granulomatous disease, hypersensitivity pneumonitis, histoplasmosis, tuberculosis, cryptogenic fibrosing alveolitis, hereditary pulmonary disorders, such as alveolar microlithiasis and bronchiectasis, eosinophilic granuloma, lymphangioleimyomatosis, and pulmonary alveolar proteinosis disorders.

In other aspects of the present disclosure, the RNAi composition comprises an antisense RNA or siRNA that is designed to target a nucleotide sequence (or in certain cases more than one nucleotide sequence) to treat or prevent inflammatory diseases or disorders. Examples of such inflammatory diseases, disorders, or conditions that may be treated or prevented include, but are not limited to, acute and chronic inflammation such as osteoarthritis, sepsis, ARDS, immune and autoimmune disorders, rheumatoid arthritis, IBD (inflammatory bowel disease), lupus, MS, graft rejection, cirrhosis, sarcoidosis, granulomatous lesions, periodontitis/gingivitis, graft-vs.-host disease, contact dermatitis, hepatitis, inflammatory brain disease, inflammatory demyelinating disease, inflammatory vasculitis, inflammatory myopathies, osteomyelitis, Crohn's disease, refractory ulcerative colitis, non-specific ulcerative colitis, interstitial cystitis, myocardial diseases, infectious diseases, pulmonary diseases and graft rejection. Autoimmune disorders that may be treated using the present compositions include, but are not limited to, chronic active hepatitis, Graves' disease, insulin-dependent diabetes mellitus (type I), and Hashimoto's thyroiditis.

In further aspects of the present disclosure, the RNAi composition comprises an antisense RNA or siRNA that is designed to target a nucleotide sequence (or in certain cases more than one nucleotide sequence) to treat or prevent respiratory diseases, including, but not limited to, asthma, allergic disorder, emphysema, adult respiratory distress syndrome (ARDS), lung reperfusion injury, ischemia-reperfusion injury of the lung, kidney, heart, and gut, and lung tumor growth and metastasis. The compositions and methods provided are also useful for treating or preventing lung diseases, including, but not limited to, diseases caused by viruses including, but not limited to, influenza virus, respiratory syncytial virus, and SARS virus, chronic obstructive pulmonary disease/disorder (COPD), pulmonary fibrosis, specifically Bleomycin-induced fibrosis, interstitial lung disease, fibrosis, restrictive lung disease, mesothelioma, pneumonia, sarcoidosis and cystic fibrosis.

In certain other embodiments of the present disclosure, the RNAi composition comprises an antisense RNA or siRNA that is designed to target a nucleotide sequence (or in certain cases more than one nucleotide sequence) to treat or prevent dermatological disorders. Such dermatological disorders include, but are not limited to, vitiligo, melanoma, dysplasic nevi, seborrheic keratoses, acanthosis nigricans, adnexal tumors, other epidermal tumors (actinic keratosis, squamous cell carcinoma, basal cell carcinoma, merkel cell carcinoma, histiocytosis X, mycosis fungoides/cutaneous T-cell lymphoma), mastocytosis, eczema/acute eczematous dermatitis, urticaria, erythema multiforme, psoriasis, lichen planus, lupus/systemic lupus erythematosus, bussous diseases, acne vulgaris, and panniculitis.

In further embodiments of the present disclosure, the RNAi composition comprises an antisense RNA or siRNA that is designed to target and silence specific splice isoforms that are linked to human diseases.

Cell-Specific Targeting or Expression

In certain aspects of the present disclosure, it is desirable to target the RLIP76 proteoliposome compositions to a specific cell-type. In certain of these "cell-specific" embodiments, the RLIP76 proteoliposomes further comprise a cell-specific targeting moiety. The cell-specific targeting moiety confers cell-type specific binding to the RLIP76 proteoliposome, and is chosen on the basis of the particular cell population to be targeted. A wide variety of compositions are suitable for use as cell-specific targeting moieties, including, but not limited to, ligands for receptors such as growth factors, hormones and cytokines, and antibodies or antigen-binding fragments thereof.

Since a large number of cell surface receptors have been identified in hematopoietic cells of various lineages, ligands or antibodies specific for these receptors may be used as cell-specific targeting moieties. IL2 may be used as a cell-specific targeting moiety to target $IL2R^+$ cells. Alternatively, other molecules such as B7-1, B7-2 and CD40 may be used to specifically target activated T cells. Furthermore, B cells express CD19, CD40 and IL4 receptor and may be targeted by moieties that bind these receptors, such as CD40 ligand, IL4, IL5, IL6 and CD28. The elimination of immune cells such as T cells and B cells is particularly useful in the treatment of autoimmunity, hypersensitivity, transplantation rejection responses and in the treatment of lymphoid tumors. Examples of autoimmune diseases are multiple sclerosis, rheumatoid arthritis, insulin-dependent diabetes mellitus, systemic lupus erythemotisis, scleroderma, and uviatis. More specifically, since myelin basic protein is known to be the major target of immune cell attack in multiple sclerosis, this protein may be used as a cell-specific targeting moiety for the treatment of multiple sclerosis (see, for example, International Patent Application Publication No. WO 97/19179).

Other cytokines that may be used to target specific cell subsets include the interleukins (IL1 through IL15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor. Other cytokines include hematopoietins (four-helix bundles) (such as Epo (erythropoietin), IL-2 (T-cell growth factor), IL-3 (multicolony CSF), IL-4 (BCGF-1, BSF-1), IL-5 (BCGF-2), IL-6 IL-4 ($IFN\beta_2$, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β); immunoglobin superfamily (such as B7.1 (CD80), and B7.2 (B70, CD86)); TNF family (such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)); and those unassigned to a particular family (such as TGF-β, IL-1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)).

Additionally, certain cell surface molecules are highly expressed in tumor cells, including, but not limited to, hormone receptors such as human chorionic gonadotropin receptor and gonadotropin releasing hormone receptor. Therefore, the corresponding hormones may be used as the cell-specific targeting moieties in cancer therapy.

In some embodiments of the present disclosure, antibodies are extremely versatile and useful cell-specific targeting moieties because they can be generated against any cell surface antigen of interest. Monoclonal antibodies have been generated against cell surface receptors, tumor-associated antigens, and leukocyte lineage-specific markers such as CD antigens. Antibody variable region genes can be readily isolated from hybridoma cells by methods well-known in the art.

Over the past few years, several monoclonal antibodies have been approved for therapeutic use and have achieved significant clinical and commercial success. Much of the clinical utility of monoclonal antibodies results from the affinity and specificity with which they bind to their targets, as well as long circulating life due to their relatively large size. Monoclonal antibodies, however, are not well suited for use in indications where a short half-life is advantageous or where their large size inhibits them physically from reaching the area of potential therapeutic activity.

Single chain antibodies (SCAs) are genetically engineered proteins designed to expand on the therapeutic and diagnostic applications possible with monoclonal antibodies. SCAs have the binding specificity and affinity of monoclonal antibodies and, in their native form, are about one-fifth to one-sixth of the size of a monoclonal antibody, typically giving them very short half-lives. Human SCAs offer many benefits compared to most monoclonal antibodies, including more specific localization to target sites in the body, faster clearance from the body, and a better opportunity to be used orally, intranasally, transdermally or by inhalation. In addition to these benefits, fully-human SCAs can be isolated directly from human SCA libraries without the need for costly and time consuming "humanization" procedures.

The variable regions from the heavy and light chains (VH and VL) are both approximately 110 amino acids long. They can be linked by a 15 amino acid linker, which has sufficient flexibility to allow the two domains to assemble a functional antigen binding pocket. In specific embodiments, addition of various signal sequences allows the scFv to be targeted to different organelles within the cell, or to be secreted. Addition of the light chain constant region (Ck) allows dimerization via disulfide bonds, giving increased stability and avidity. Thus, for a single chain Fv (scFv) SCA, although the two domains of the Fv fragment are coded for by separate genes, it has been proven possible to make a synthetic linker that enables them to be made as a single protein chain scFv by recombinant methods. Furthermore, they are frequently used due to their ease of isolation from phage display libraries and their ability to recognize conserved antigens. For example, scFv is utilized to target suicide genes to carcinoembryonic antigen (CEA)-expressing tumor cells by a retrovector displaying anti-CEA scFv.

Finally, the Fc portion of the heavy chain of an antibody may be used to target Fc receptor-expressing cells such as the use of the Fc portion of an IgE antibody to target mast cells and basophils. The use of antibodies to target a polypeptide or peptide of interest by antibody-directed therapy or immunological-directed therapy is currently approved and in use in the present therapeutic market.

In other aspects of the present disclosure, the nucleic acid cargo molecule is operably linked to a tissue-specific promoter, which results in tissue-specific expression of the nucleic acid cargo molecule (see, e.g., U.S. Patent Application Publication No. 20080131940), or operably linked to a cell-specific transcription response element, which results in expression of the nucleic acid cargo molecule in specific cell-types (see, e.g., U.S. Pat. No. 6,991,935).

Pharmaceutical Compositions and Routes of Administration

Preventative or therapeutic formulations are provided as pharmaceutical preparations for local administration to patients or subjects. The term "patient" or "subject" as used herein refers to human or animal subjects (animals being particularly useful as models for clinical efficacy of a particular composition). Selection of a suitable pharmaceutical preparation depends upon the method of administration chosen, and may be made according to protocols well-known to medicinal chemists.

As used herein, a "dosage unit" is a RLIP76 proteoliposome comprising one or more cargo molecules in a pharmaceutically acceptable carrier. The term "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the RLIP76 proteoliposome or cargo molecules, its use in the therapeutic compositions is contemplated. Supplementary active ingredients or therapeutic agents can also be incorporated into the RLIP76 proteoliposome compositions.

As used herein, "pharmaceutically-acceptable salts" refer to derivatives of the disclosed compounds wherein one or more components of the disclosed compounds is modified by making acid or base salts thereof. Examples of pharmaceutically-acceptable salts include, but are not limited to: mineral or organic acid salts of basic residues such as amines; alkali or organic salts of acidic residues such as carboxylic acids; and the like. Thus, the term "acid addition salt" refers to the corresponding salt derivative of a component that has been prepared by the addition of an acid. The pharmaceutically-acceptable salts include the conventional salts or the quaternary ammonium salts of the component formed, for example, from inorganic or organic acids. For example, such conventional salts include, but are not limited to: those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds may exist as zwitterions. All forms of the active agents, including free acid, free base, and zwitterions, are contemplated to be within the scope of the present disclosure.

A protein can be formulated into a composition in a neutral or salt form. Pharmaceutically acceptable salts include the acid addition salts (formed with the free amino groups of the protein), and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In addition, the disclosed compositions or components thereof can be complexed with polyethylene glycol (PEG), metal ions, or incorporated into polymeric compounds such as polylactic acid, polyglycolic acid, hydrogels, dextran, and the like. Such compositions will influence the physical state, solubility, stability, rate of in vivo release, and rate of in vivo clearance, and are thus chosen according to the intended application.

The disclosed compounds can be orally administered, for example, with an inert diluent or with an assimilable edible carrier, or they can be enclosed in hard or soft shell gelatin capsule, or they can be incorporated directly with the food of the diet. For oral therapeutic administration, the disclosed compounds can be incorporated with excipients and used in the form of ingestible, buccal tablets, troches, capsules, elixirs, suspensions, syrups, wafers, and the like. Such compositions and preparations should contain at least 0.1% of disclosed compound. The percentage of the compositions and preparations may, of course, be varied and may conveniently be between about 2 to about 60% of the weight of the unit. The amount of disclosed compounds in such therapeutically useful compositions is such that a suitable dosage will be obtained.

When the form of the dosage unit is a tablet, troche, pill, capsule and the like, it may also contain one or more of the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. When the form of the dosage unit is a syrup or elixir, it may contain sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the form of the dosage unit may be a sustained-release, extended-release, or delayed-release preparation or formulation.

The disclosed compounds may also be administered parenterally or intraperitoneally. Solutions of the dosage unit can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion (see, for example, "Remington's Pharmaceutical Sciences" 15th Edition, pages 1035-1038 and 1570-1580 (Osol and Hoover, eds., Mack Publishing Company, Easton, Pa., 1975)). Some variation in dosage will necessarily occur depending on the condition of the subject being treated. The person responsible for administration will, in any event, determine the appropriate dose for the individual subject.

The dosage unit forms suitable for injectable use include sterile aqueous solutions or dispersions and sterile powders for the extemporaneous preparation of sterile injectable solutions or dispersions. In all cases the form must be sterile and must be suitably fluid. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the disclosed compounds in the required amount in the appropriate solvent with various of the other ingredients enumerated above, as required, followed by filtered sterilization. Generally, dispersions are prepared by incorporating the various sterilized ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques, which yield a powder of the dosage unit plus any additional desired ingredient from a previously sterile-filtered solution thereof.

In certain embodiments the disclosed compositions can be formulated to be administered by use of a skin patch, or transdermal delivery system. Transdermal administration can be accomplished by any of a number of systems known in the art. Examples of systems that may be adapted for use with the compositions described herein include, but are not limited to, those systems of transdermal administration described in U.S. Pat. Nos. 4,816,252, 5,122,382, 5,198,223, 5,023,084, 4,906,169, 5,145,682, 4,624,665, 4,687,481, 4,834,978, and 4,810,499. These methods typically include an adhesive matrix or drug reservoir system and may include a skin permeation enhancement agent such as ethanol, polyethylene glycol 200 dilaurate, isopropyl myristate, glycerol trioleate, linolenic acid saturated ethanol, glycerol monooleate, glycerol monolaurate, n-decyl alcohol, capric acid, and certain saturated and unsaturated fatty acids, and their esters, alcohols, monoglycerides, acetate, diethanolamides and N,N-dimethylamides (see, for example, U.S. Pat. No. 4,906,169).

In other aspects, the disclosed compositions can be formulated for respiratory, pulmonary, or nasal administration.

Effective Dose

In certain aspects the present disclosure encompasses methods of treating, managing, and/or preventing a disease or disorder, which comprise administering to a patient in need of such treatment, management, or prevention a therapeutically or prophylactically effective amount of a disclosed composition or dosage unit thereof. In certain embodiments, such a compound or dosage unit is referred to as an active agent. Use of the disclosed compositions in the manufacture of a medicament for treating or preventing a disease or disorder is also contemplated. The present disclosure also encompasses compositions comprising a biologically or therapeutically effective amount of one or more cargo molecules for use in the preparation of a medicament for use in prevention and/or treatment of a disease or disorder.

As used herein, and unless otherwise indicated, the terms "treat," "treating," and "treatment" contemplate an action that occurs while a patient is suffering from a disease or disorder, that reduces the severity of one or more symptoms or effects of the disease or disorder, or a related disease or disorder. As used herein, and unless otherwise indicated, the terms "prevent," "preventing," and "prevention" contemplate an action that occurs before a patient begins to suffer from a disease or disorder, that prolongs the onset of, and/or inhibits or reduces the severity of, the disease or disorder. As used herein, and unless otherwise indicated, the terms "manage," "managing," and "management" encompass preventing, delaying, or reducing the severity of a recurrence of a disease or disorder in a patient who has already suffered from the disease or disorder. The terms encompass modulating the threshold, development, and/or duration of the disease or disorder, or changing the way that a patient responds to the disease or disorder.

As used herein, and unless otherwise specified, a "therapeutically effective amount" of a compound is an amount sufficient to provide any therapeutic benefit in the treatment or management of a disease or disorder, or to delay or minimize one or more symptoms associated with a disease or disorder. A therapeutically effective amount of a compound means an amount of the compound, alone or in combination with one or more other therapy and/or therapeutic agent, which provides any therapeutic benefit in the treatment or management of a disease or disorder, or related diseases or disorders. The term "therapeutically effective amount" can encompass an amount that cures a disease or disorder, improves or reduces a disease or disorder, reduces or avoids symptoms or causes of a disease or disorder, improves overall therapy, or enhances the therapeutic efficacy of another therapeutic agent.

As used herein, and unless otherwise specified, a "prophylactically effective amount" of a compound is an amount sufficient to prevent or delay the onset of a disease or disorder, or one or more symptoms associated with a disease or disorder, or prevent or delay its recurrence. A prophylactically effective amount of a compound means an amount of the compound, alone or in combination with one or more other treatment and/or prophylactic agent, which provides a prophylactic benefit in the prevention of a disease or disorder. The term "prophylactically effective amount" can encompass an amount that prevents a disease or disorder, improves overall prophylaxis, or enhances the prophylactic efficacy of another prophylactic agent.

Toxicity and therapeutic efficacy of the described compounds and compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, expressed as the ratio LD50/ED50. Compounds that exhibit large therapeutic indices are preferred. Compounds that exhibit toxic side effects may be used in certain embodiments, however, care should usually be taken to design delivery systems that target such compounds preferentially to the site of affected tissue, in order to minimize potential damage to uninfected cells and, thereby, reduce side effects.

Data obtained from cell culture assays and animal studies can be used in formulating a range of dosages for use in humans. In certain aspects of the present disclosure, the dosages of such compounds lie within a range of circulating concentrations that include the ED50 with little or no toxicity. The dosage may vary within this range depending on the dosage form employed and the route of administration utilized. For any compound used in the disclosed methods, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Plasma levels may be measured, for example, by high performance liquid chromatography.

When therapeutic treatment is contemplated, the appropriate dosage may also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies help establish safe doses. Additionally, the bioactive agent may be complexed with a variety of well established compounds or structures that, for instance, enhance the stability of the bioactive agent, or otherwise enhance its pharmacological properties (e.g., increase in vivo half-life, reduce toxicity, etc.).

In certain embodiments of the present disclosure, the effective dose of the composition or dosage unit can be in the range of about 10 mg/kg to about 0.01 mg/kg, about 10 mg/kg to about 0.025 mg/kg, about 10 mg/kg to about 0.05 mg/kg, about 10 mg/kg to about 0.1 mg/kg, about 10 mg/kg to about 0.25 mg/kg, about 10 mg/kg to about 0.5 mg/kg, about 10 mg/kg to about 1 mg/kg, about 10 mg/kg to about 2.5 mg/kg, about 10 mg/kg to about 5 mg/kg, about 5 mg/kg to about 0.01 mg/kg, about 2.5 mg/kg to about 0.01 mg/kg, about 1 mg/kg to about 0.01 mg/kg, about 0.5 mg/kg to about 0.01 mg/kg, about 0.25 mg/kg to about 0.01 mg/kg, about 0.1 mg/kg to about 0.01 mg/kg, about 0.05 mg/kg to about 0.01 mg/kg, about 0.025 mg/kg to about 0.01 mg/kg, about 5 mg/kg to about 0.025 mg/kg, about 2.5 mg/kg to about 0.05 mg/kg, about 1 mg/kg to about 0.1 mg/kg, about 0.5 mg/kg to about 0.25 mg/kg, or about 3 mg/kg to about 0.1 mg/kg, or so. Thus, in particular embodiments, the effective dose of the composition or dosage unit is about 0.01 mg/kg, about 0.025 mg/kg, about 0.05 mg/kg, about 0.075 mg/kg, about 0.1 mg/kg, about 0.25 mg/kg, about 0.5 mg/kg, about 0.75 mg/kg, about 1 mg/kg, about 2.5 mg/kg, about 3 mg/kg, about 5 mg/kg, about 7.5 mg/kg, or about 10 mg/kg, or so.

Kits

In some cases, the disclosed active ingredients are preferably not administered to a patient at the same time or by the same route of administration. This disclosure therefore encompasses kits that, when used by the medical practitioner, can simplify the administration of appropriate amounts of active ingredients to a patient.

A typical kit comprises a single dosage unit form of one or more of the disclosed compounds, or a pharmaceutically acceptable salt, prodrug, solvate, hydrate, or stereoisomer thereof. In certain embodiments, a single dosage unit form of another agent that may be used in combination with the disclosed compounds. Kits of the current disclosure can further comprise devices that are used to administer the active ingredients. Examples of such devices include, but are not limited to, syringes, drip bags, patches, and inhalers.

The disclosed kits can further comprise pharmaceutically acceptable vehicles that can be used to administer one or more disclosed compositions. For example, if a disclosed composition is provided in a solid form that is to be reconstituted for parenteral administration, the kit can comprise a sealed container of a suitable vehicle in which the disclosed composition can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in specific embodiments, the disclosed formulations do not contain any alcohols or other co-solvents, oils or proteins.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

C57B mice that carry both copies of the RIP1 (mouse version of RLIP76) gene (wild-type; +/+), one copy of the RIP1 gene (heterozygous; +/−), or no copies of the RIP1 gene (homozygous; −/−) were created using Cre-Lox technology that can selectively suppress genes (Lexicon Genetics, Incorporated, The Woodlands, Tex.). Mice approximately ten weeks of age from mating heterozygous RIP1 by heterozygous RIP1 mice were genotyped using a PCR strategy, in which mouse tail DNA was isolated and used as a template in PCR reaction with primers upstream and downstream of the insertion site used to create the knockout RIP1 mice. The PCR product from a wild-type RIP mouse should be a 200 bp band, and the PCR product from a knockout homozygous RIP1 mouse should be a 150 bp band. The PCR product from a heterozygous RIP1 mouse should yield both bands. In FIG. 1A, lane M is a DNA ladder, lane 1 shows the result of PCR from a knockout homozygous RIP1 mouse, lane 2 shows the result of PCR from a heterozygous RIP1 mouse, lane 3 shows the result of PCR from a wild-type RIP1 mouse. From heterozygous (+/−) RIP1 mice, colonies of wild-type (+/+), heterozygous (+/−), and homozygous (−/−) RIP1 mice were established by segregation and mating of animals based on genotyping by polymerase chain reaction (PCR) on tail tissue (FIG. 1A).

Figure 1B:
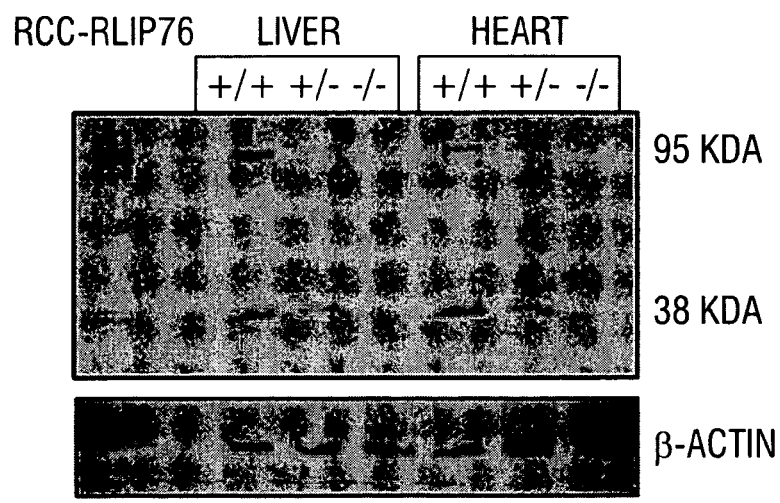

Crude membrane fractions from several tissues were prepared and subjected to SDS-PAGE with application of 100 µg protein per lane. Gels were transblotted on to nitrocellulose membranes, followed by Western blotting using anti-RLIP76 IgG as primary antibody. The blots were developed with 4-chloro-1-naphthol as chromogenic substrate. Lane 1 contained detergent extract of bacterial membranes from recombinant $E.\ coli$ expressing RLIP76 (pET-30a[+]-RLQLIP-BL21(DE3)). Lane 2 was blank. Lanes 3-5 contained membrane extract from liver, and lanes 6-8 contained membrane extract from heart. Lanes 3 and 6 contained protein from wild-type RIP1 mice, lanes 4 and 7 contained protein from heterozygous RIP1 mice, and lanes 5 and 8 contained protein from homozygous RIP1 knockout mice. β-actin expression was used as internal control. Western-blot analysis of mouse tissues using anti-RLIP76 antibodies confirmed decreased RIP1 levels in the RIP1 heterozygous (+/−) mice, and the absence of RLIP76 in tissues from the RIP1 homozygous (−/−) mice (FIG. 1B).

Figure 2A:
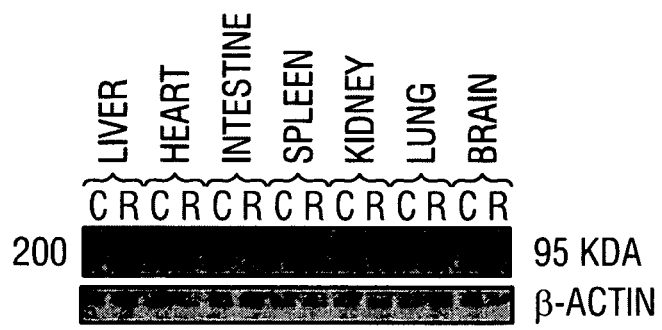
FIG. 2A and FIG. 2B. Protein distribution using RLIP76 liposomes.
Figure 2B:
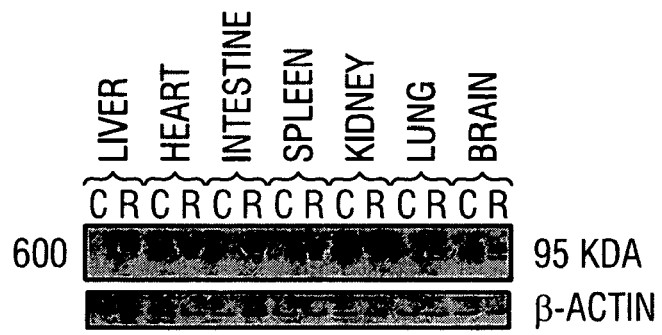

Western blot analysis of tissues from homozygous RIP1 knockout mice was performed after i.p. injection of RLIP76 liposomes. In FIG. 2A, homozygous RIP1 knockout mice were treated i.p. with RLIP76 liposomes containing 200 µg RLIP76 protein and sacrificed 48 hours later. In FIG. 2B, homozygous RIP1 knockout mice were treated with 3 doses of 200 µg RLIP76 liposomes at time 0, 72 hours, and 120 hours, followed by sacrifice at 168 hours. Lanes labeled C are from mice treated with control liposomes without RLIP76, and lanes labeled R are from mice treated with RLIP76-liposomes. The indicated tissues were homogenized, and aliquots of the detergent solubilized crude membrane fraction containing 200 µg protein was subjected to SDS-PAGE, transblotted to nitrocellulose membrane, and detected using anti-RLIP76 as primary antibody and peroxidase-conjugated goat-anti-rabbit IgG as secondary antibody. The blots were developed with 4-chloro-1-napthol, and β-actin expression was used as a loading control. A single dose of RLIP76-liposomes containing 200 µg purified RLIP76 administered i.p. followed 48 hours later by sacrificing the animals and analyzing tissues immunologically for presence of RLIP76 showed convincingly that these liposomes could be used to deliver RLIP76 to all tissues of homozygous RIP1−/− mice tested, including brain (FIG. 2A). Administration of 3 doses of RLIP76-liposomes at the same dose over 8 days followed by sacrifice at day 10 showed further accumulation of RLIP76 in the homozygous RIP1 mouse tissues (FIG. 2B).

These Western-blot analyses confirmed the lack of any detectable RIP1 in any tissue tested from the homozygous RIP1 mice, and the presence of a band at the expected $M_r$ of 95 kDa for intact RLIP76 in all tissues examined from mice treated with RLIP76 liposomes. The 38 kDa band represents a C-terminal proteolytic fragment of RLIP76 beginning at amino acid 424. Remarkably, even the brain tissue took up a significant amount of RLIP76, a finding that has significant pharmacological implications for delivery of drugs to the brain and other organs.

Example 2

A study was conducted in a mouse model for the ability of RLIP liposomes to deliver a nucleic acid cargo molecule to various tissues when administered orally. The nucleic acid is DN5, an antisense oligomer to the SET-1 gene. Expression in various tissues tested was detected by RT-PCR and Western blot in samples 24 and 72 hours post administration.

Mice were given 100 µg orally of the specified agent in each study. Animals were sacrificed either 24 or 72 hours after administration and tissue sampled for mRNA expression to the gene of interest by RT-PCR technique. In the graphs, the density of each band has been quantitated with image analysis software and corrected for differences in background and loading (standardizing to the actin bands in each lane). The units on the Y axis are pixel counts for each band on the gel. DN5 is an antisense oligomer to the SET-1 gene, and R508 is an antisense oligomer to RLIP76 (used as a control).

Figure 3A:
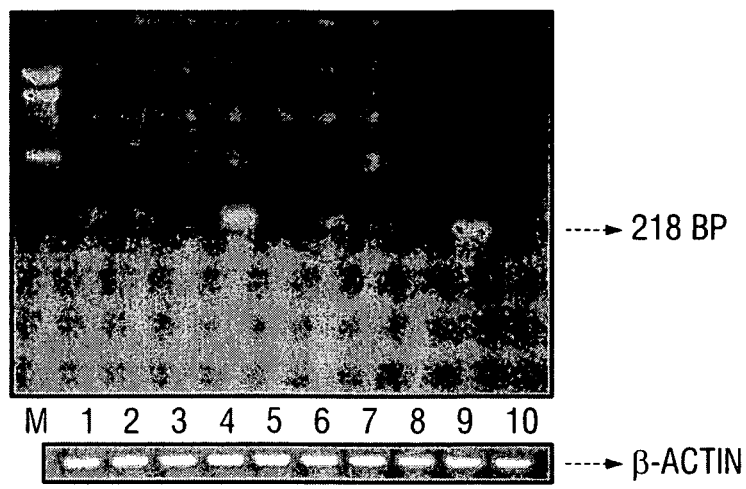
FIG. 3A, FIG. 3B, and FIG. 3C are data from control experiments in which mice were fed empty liposomes (FIG. 3A), liposomes containing the R508 nucleic acid (antisense to RLIP76) (FIG. 3B), and the R508 nucleic acid in combination with RLIP76 liposomes (FIG. 3C). Expression of SET-1 mRNA in lung (lanes 1 and 6), liver (lanes 2 and 7), heart (lanes 3 and 8), brain (lanes 4 and 9), and kidney (lanes 5 and 10) tissues is detected by RT-PCR analysis 24 (lanes 1-5) and 72 hours (lanes 6-10) after ingestion.
Figure 3B:
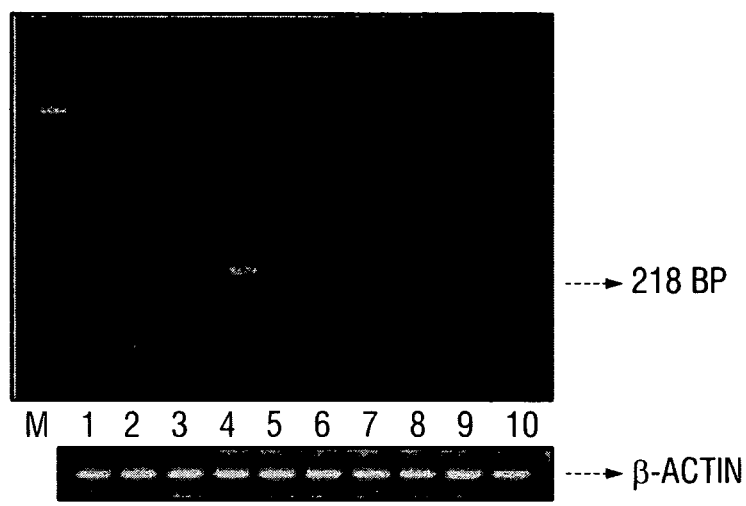
Figure 3C:
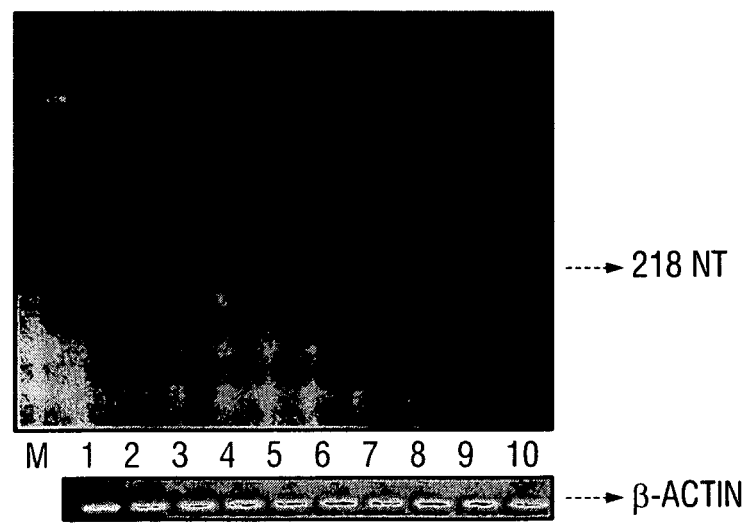

FIG. 3A shows the results from wild-type mice treated with control liposomes of expression of SET-1 mRNA in lung (lanes 1 and 6), liver (lanes 2 and 7), heart (lanes 3 and 8), brain (lanes 4 and 9), and kidney (lanes 5 and 10) tissues detected by RT-PCR analysis of animals sacrificed at 24 hours (lanes 1-5) and 72 hours (lanes 6-10) after treatment. The SET-1 forward primer was based on nucleotides 1422-1440 of the SET-1 coding sequence, and the SET-1 reverse primer was based on nucleotides 1621-1640 of the SET-1 coding sequence. Expression of β-actin was used as an internal control. The β-actin forward primer was based on nucleotides 748-767 of the β-actin coding sequence, and the β-actin reverse primer was based on nucleotides 1174-1193 of the β-actin coding sequence. FIG. 3B shows the results from wild-type mice treated with 100 µg of R508 in control liposomes of expression of SET-1 mRNA in lung (lanes 1 and 6), liver (lanes 2 and 7), heart (lanes 3 and 8), brain (lanes 4 and 9), and kidney (lanes 5 and 10) tissues detected by RT-PCR analysis of animals sacrificed 24 hours (lanes 1-5) and 72 hours (lanes 6-10) after treatment. FIG. 3C shows the results from wild-type mice treated with 100 μg of R508 along with 100 μg of RLIP76 liposomes of expression of SET-1 mRNA in lung (lanes 1 and 6), liver (lanes 2 and 7), heart (lanes 3 and 8), brain (lanes 4 and 9), and kidney (lanes 5 and 10) tissues detected by RT-PCR analysis of animals sacrificed 24 hours (lanes 1-5) and 72 hours (lanes 6-10) after treatment. The results show that the RLIP76 antisense oligomer has no effect on SET-1 mRNA expression.

Figure 4A:
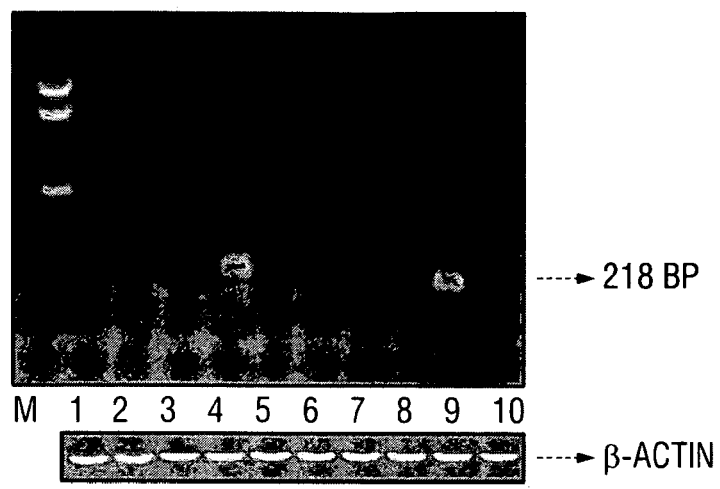
FIG. 4A and FIG. 4B are data from a study in which mice were treated with the DN5 nucleic acid (antisense to SET-1) in a control liposome (FIG. 4A) and an RLIP76 liposome (FIG. 4B). Expression of SET-1 mRNA in lung (lanes 1 and 6), liver (lanes 2 and 7), heart (lanes 3 and 8), brain (lanes 4 and 9), and kidney (lanes 5 and 10) tissues is detected by RT-PCR analysis 24 (lanes 1-5) and 72 hours (lanes 6-10) after ingestion.
Figure 4B:
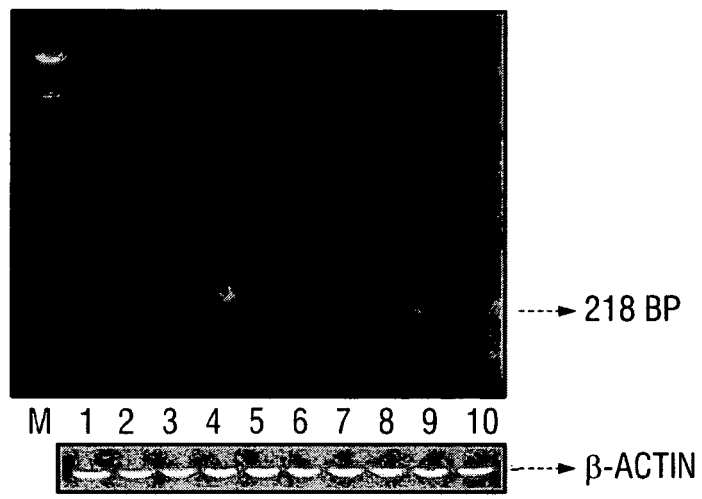

FIG. 4A shows the results from wild-type mice treated with 100 μg of DN5 in control liposomes of expression of SET-1 mRNA in lung (lanes 1 and 6), liver (lanes 2 and 7), heart (lanes 3 and 8), brain (lanes 4 and 9), and kidney (lanes 5 and 10) tissues detected by RT-PCR analysis of animals sacrificed 24 hours (lanes 1-5) and 72 hours (lanes 6-10) after treatment. FIG. 4B shows the results from wild-type mice treated with 100 μg of DN5 along with 100 μg of RLIP76 liposomes of expression of SET-1 mRNA in lung (lanes 1 and 6), liver (lanes 2 and 7), heart (lanes 3 and 8), brain (lanes 4 and 9), and kidney (lanes 5 and 10) tissues detected by RT-PCR analysis of animals sacrificed 24 hours (lanes 1-5) and 72 hours (lanes 6-10) after treatment. The results show that while delivery of the SET-1 antisense oligomer in control liposomes does not have a drastic effect on SET-1 mRNA expression, delivery of the SET-1 antisense oligomer in RLIP76 liposomes leads to a marked reduction in SET-1 mRNA expression.

Figure 5:
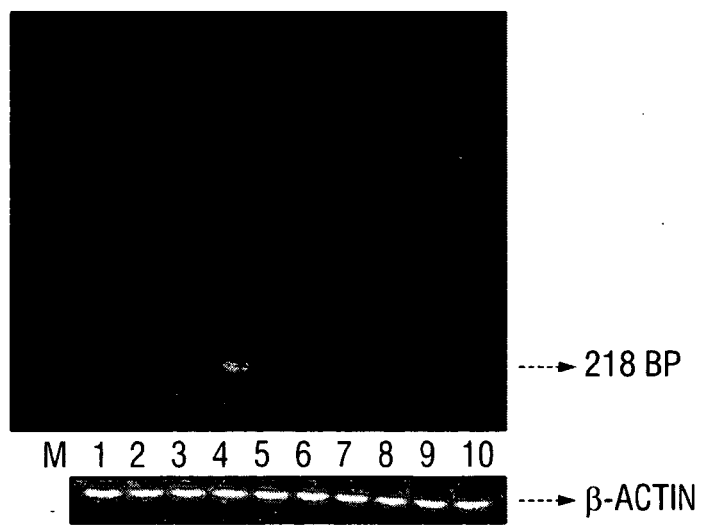
FIG. 5 is data from a study in which mice were treated with DN5 (antisense to SET-1) in a control liposome (lanes 1-5) and an RLIP76 liposome (lanes 6-10). Expression of SET-1 mRNA in lung (lanes 1 and 6), liver (lanes 2 and 7), heart (lanes 3 and 8), brain (lanes 4 and 9), and kidney (lanes 5 and 10) tissues is detected by RT-PCR analysis 24 hours after ingestion.

This can be seen even more clearly in FIG. 5. FIG. 5 shows the results from wild-type mice treated with 200 μg of DN5 in control liposomes (lanes 1-5) and wild-type mice treated with 200 μg of DN5 in 1 mg of RLIP76 liposomes (lanes 6-10) of expression of SET-1 mRNA in lung (lanes 1 and 6), liver (lanes 2 and 7), heart (lanes 3 and 8), brain (lanes 4 and 9), and kidney (lanes 5 and 10) tissues detected by RT-PCR analysis of animals sacrificed 24 hours after treatment. While SET-1 mRNA expression is clearly seen in lung, liver, and brain when the SET-1 antisense oligomer was delivered in control liposomes, expression of SET-1 mRNA in lung and liver is barely detectable when the SET-1 antisense oligomer was delivered in RLIP76 liposomes, and expression of SET-1 mRNA is brain is greatly reduced.

Figure 6:
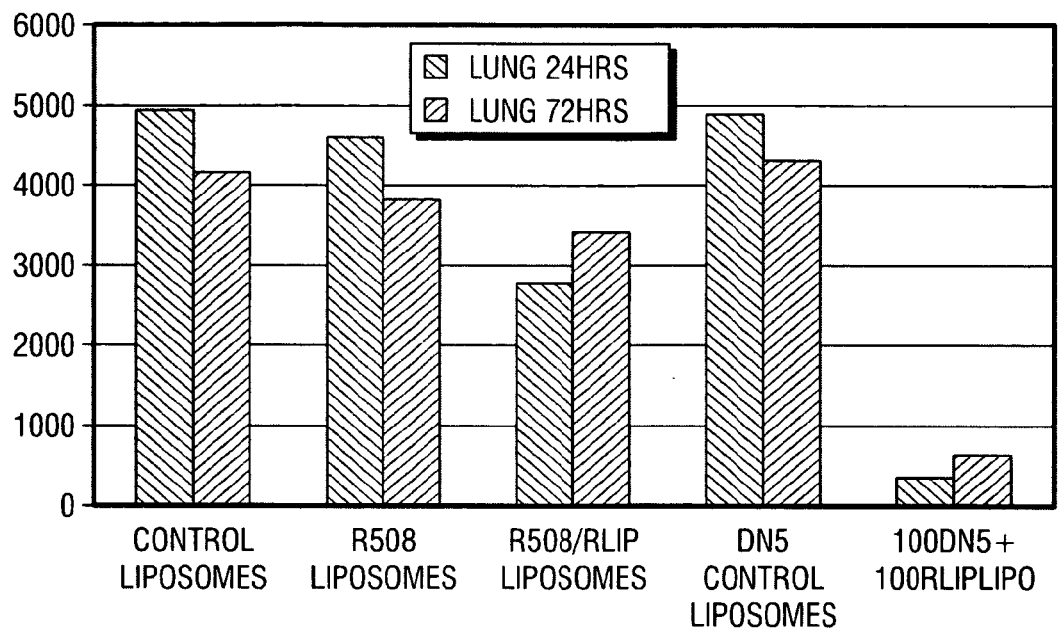
FIG. 6 is a graph of a summary of data for expression of SET-1 mRNA in lung 24 and 72 hours after treatment with control (empty) liposomes, liposomes containing the R508 nucleic acid, RLIP76 liposomes containing the R508 nucleic acid, liposomes containing the DN5 nucleic acid, and RLIP76 liposomes containing the DN5 nucleic acid.
Figure 7:
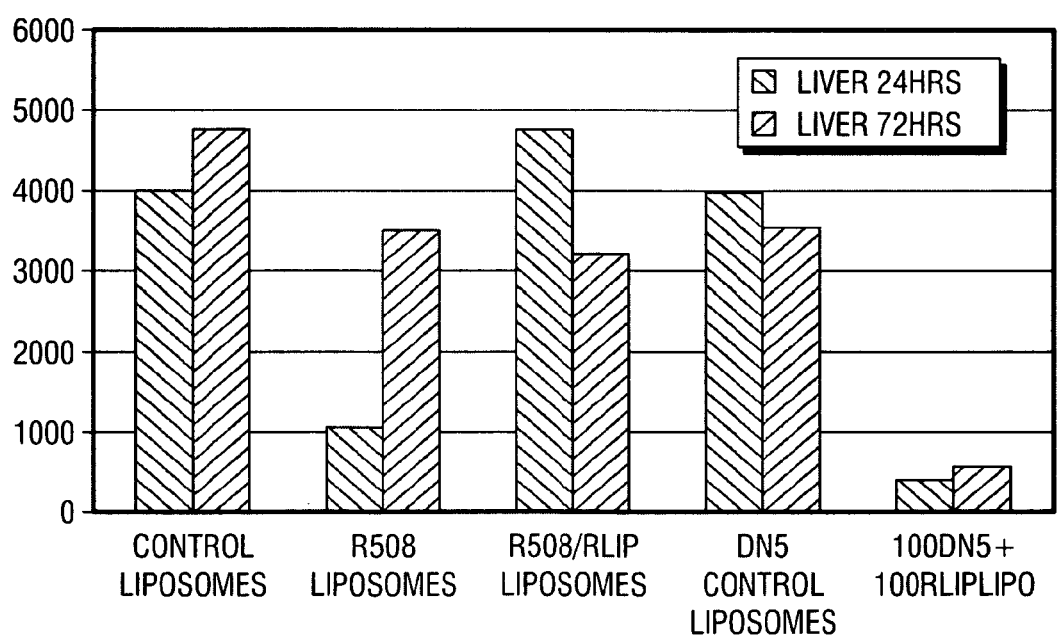
FIG. 7 is a graph of a summary of data for expression of SET-1 mRNA in liver 24 and 72 hours after treatment with control (empty) liposomes, liposomes containing the R508 nucleic acid, RLIP76 liposomes containing the R508 nucleic acid, liposomes containing the DN5 nucleic acid, and RLIP76 liposomes containing the DN5 nucleic acid.
Figure 8:
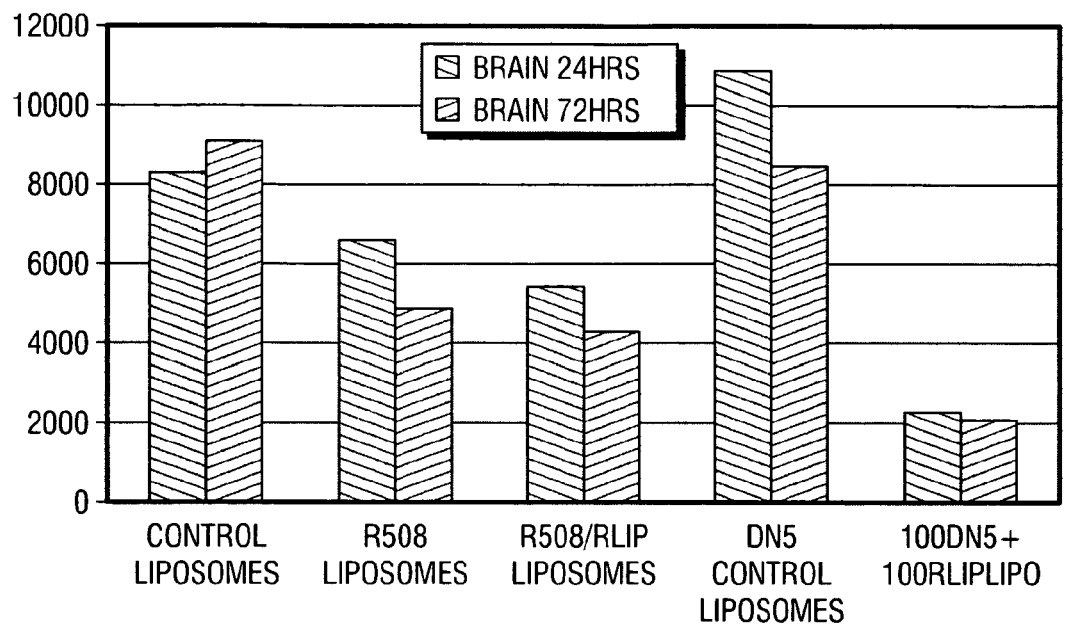
FIG. 8 is a graph of a summary of data for expression of SET-1 mRNA in brain 24 and 72 hours after treatment with control (empty) liposomes, liposomes containing the R508 nucleic acid, RLIP76 liposomes containing the R508 nucleic acid, liposomes containing the DN5 nucleic acid, and RLIP76 liposomes containing the DN5 nucleic acid.
Figure 9:
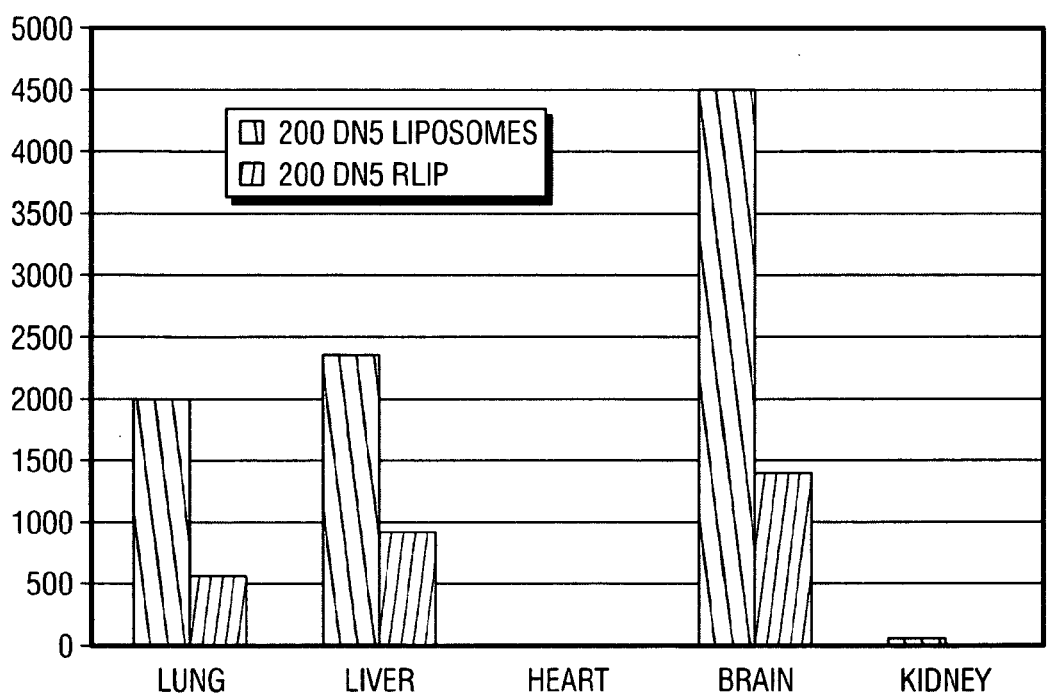
FIG. 9 is a graph of a summary of data showing SET-1 mRNA expression in lung, liver, heart, brain, and kidney 24 hours after an oral dose of liposomes containing 200 µg of the DN5 nucleic acid, and RLIP76 liposomes containing 200 µg of the DN5 nucleic acid.

The results shown in the graphs in FIG. 6-8 clearly show that with oral delivery, there is a substantial advantage to the RLIP76 liposomes in terms of functional delivery of the antisense oligomer to the lungs (FIG. 6), liver (FIG. 7) and brain (FIG. 8) of the mice, as all those tissues exhibited a significant decrease in expression of the SET-1 gene after delivery of the antisense oligomer in RLIP liposomes compared to delivery in control liposomes. FIG. 9 shows SET-1 mRNA expression levels in wild-type mice 24 hours after an oral dose of 200 μg of DN5 in control liposomes or 200 μg of DN5 in RLIP76 liposomes. Although there is very little expression of SET-1 in heart and kidney, SET-1 expression is greatly reduced in lung, liver, and brain tissue after delivery of the DN5 antisense oligomer in RLIP liposomes compared to the delivery of the DN5 antisense oligomer in regular liposomes. These results clearly show that with oral delivery, there is a substantial advantage to the RLIP76 liposomes in terms of functional delivery of the antisense oligomer.

Example 3

Figure 10A:
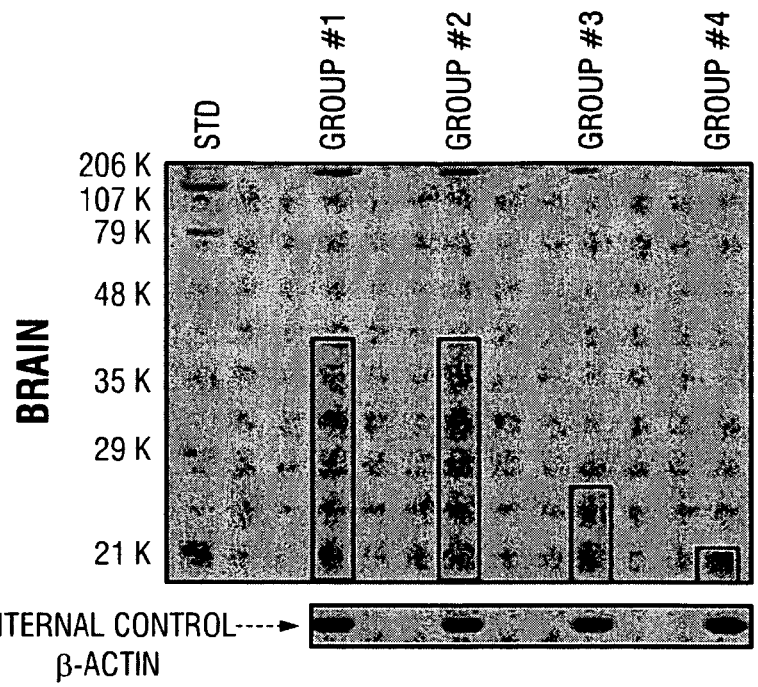
FIG. 10A, FIG. 10B, FIG. 10C, FIG. 10D, FIG. 10E, and FIG. 10F are Western blots to detect expression of SET-1 in brain (FIG. 10A, FIG. 10B, and FIG. 10C) and lung (FIG. 10D, FIG. 10E, and FIG. 10F) tissue of mice after treatment with control liposomes containing 100 µg of scrambled antisense nucleic acid (group 1), 200 µg of RLIP76 liposomes containing 100 µg of scrambled antisense nucleic acid (group 2), control liposomes containing 100 µg of DN5 antisense nucleic acid (group 3), or 200 µg of RLIP76 liposomes containing 100 µg of DN5 antisense nucleic acid (group 4).
Figure 10B:
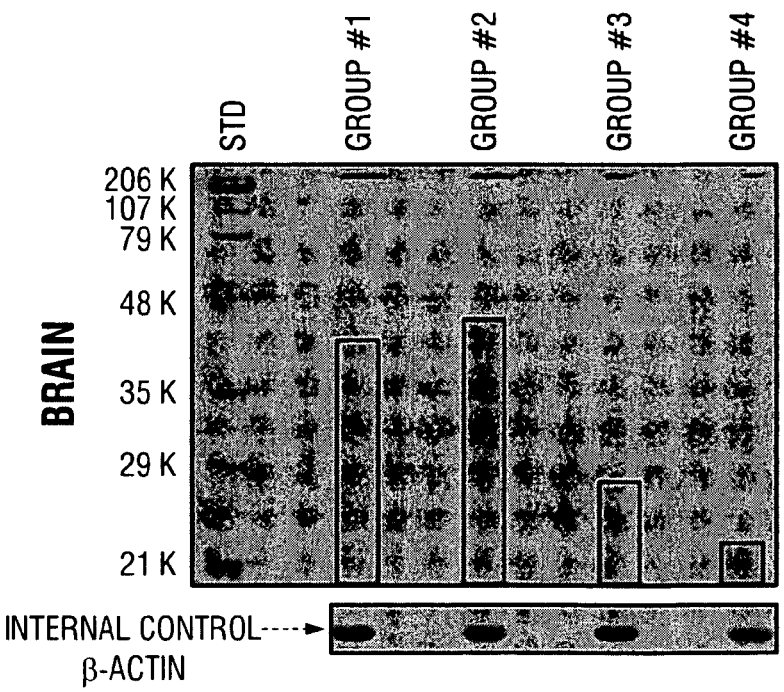
Figure 10C:
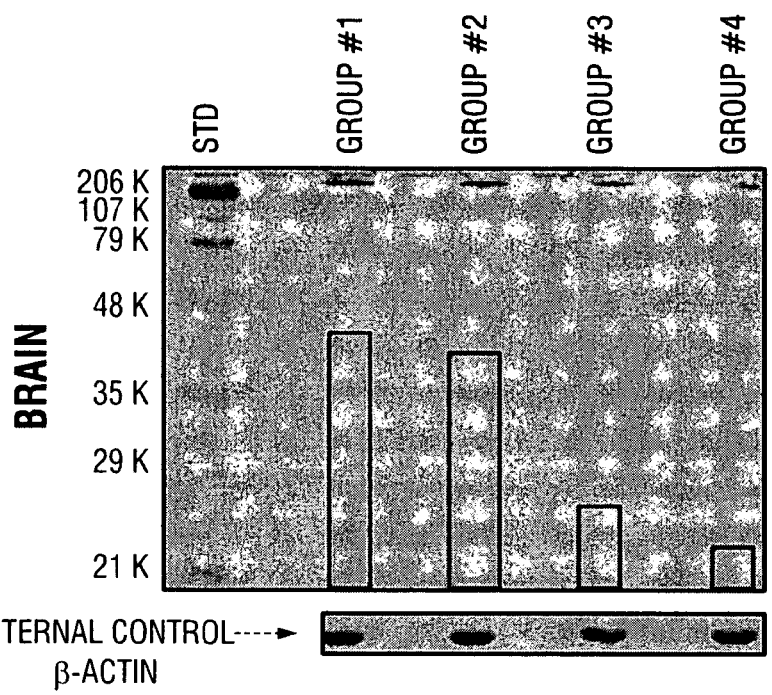
Figure 10D:
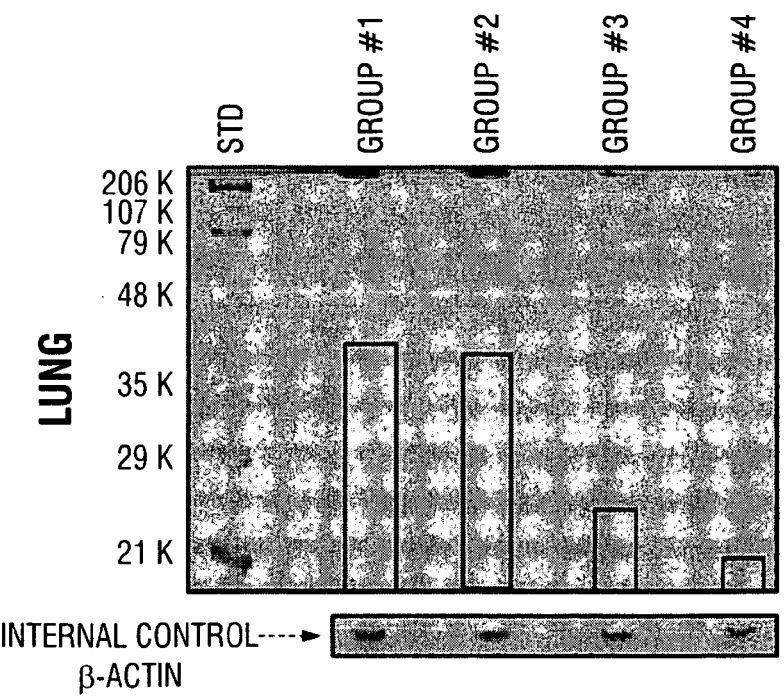
Figure 10E:
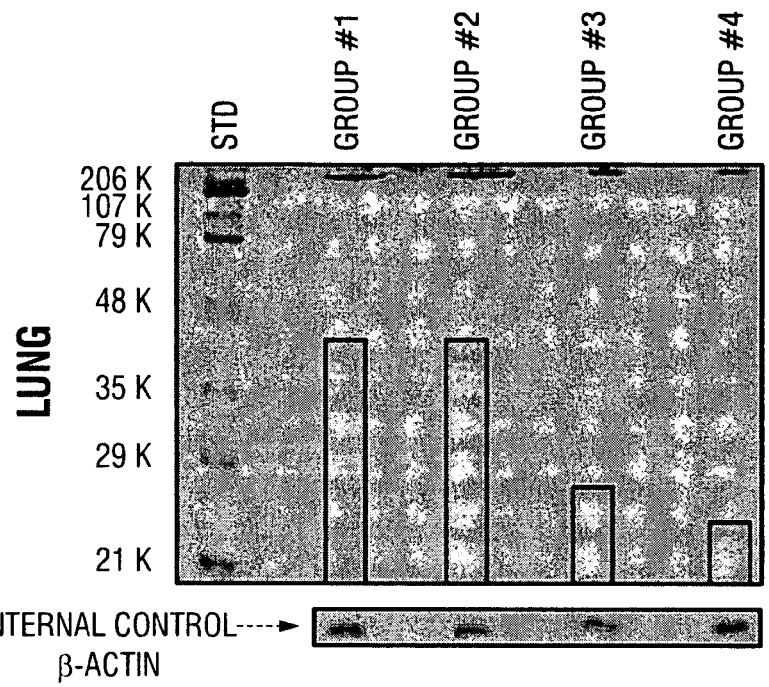
Figure 10F:
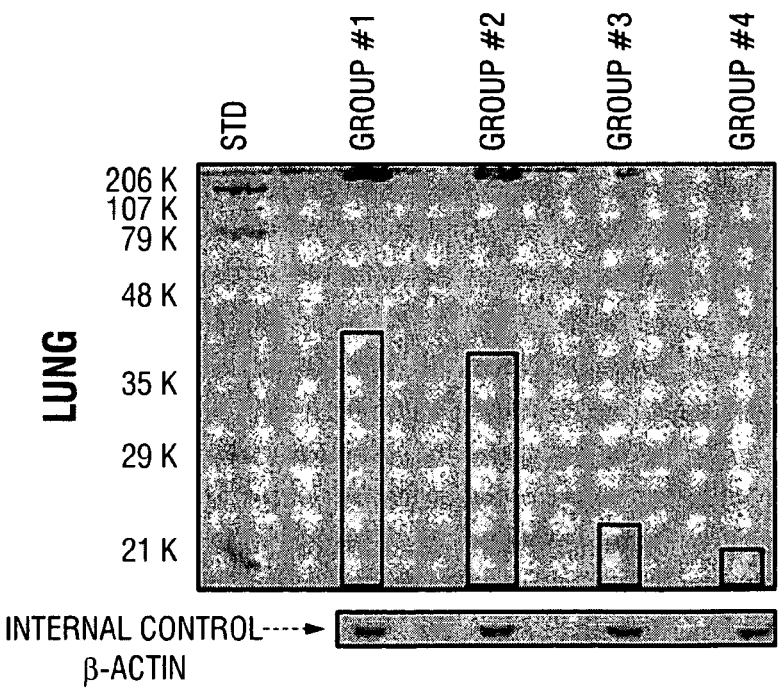

A similar study was conducted but this time immunoblotting with a monoclonal antibody to SET-1 and the liposomes were delivered via intraperitoneal administration. With this technique, there was less difference between liposomes with and without RLIP76 but the RLIP76 proteoliposomes continued to demonstrate better delivery. 200 μg crude fraction of mouse brain (FIG. 10A, FIG. 10B, and FIG. 10C) and mouse lung (FIG. 10D, FIG. 10E, and FIG. 10F) were applied to SDS-PAGE and subjected to Western blot analyses against rabbit-anti-human SET1 IgG as a primary antibody. Western blots were developed using horseradish peroxidase-conjugated goat-anti-rabbit IgG as secondary antibody. Twelve wild-type mice were divided into 4 groups of 3 animals each. Group #1 represents mice treated with 100 μg of scrambled antisense oligonucleotide plus control liposomes, Group #2 represents mice treated with 100 μg of scrambled antisense oligonucleotide plus 200 μg of RLIP76 liposomes, Group #3 represents mice treated with 100 μg of DN5 antisense oligonucleotide plus control liposomes, and Group #4 represents mice treated with 100 μg of DN5 antisense oligonucleotide plus 200 μg of RLIP76 liposomes. Bands were quantitated by scanning densitometry using β-actin as an internal control. Although a decrease in SET-1 expression is seen with delivery of the DN5 antisense oligomer by control liposomes, the decrease in expression of SET-1 after administration of the DN5 antisense oligomer in RLIP liposomes is greater than that seen after delivery in control liposomes. Thus, once again, there is an advantage to the RLIP76 liposomes in terms of functional delivery of the antisense oligomer.

Example 4

A study is conducted in a mouse model for the ability of RLIP liposomes to deliver a nucleic acid cargo molecule to various tissues when administered by i.p. injection. The nucleic acid is an siRNA molecule to the GAPDH gene. Expression in the tissues is detected by RT-PCR and Western blot in samples 24 and 72 hours post administration.

Three groups of 3 wild-type balb/c mice are administered (i.p.) with a single dose. Group 1 mice each receive 50 μg of RLIP76 proteoliposome with 100 μg siRNA targeting the GAPDH gene. Group 2 mice each receive 50 μg of RLIP76 proteoliposome with 100 μg negative control siRNA (scrambled sequence). Group 3 mice each receive liposomes alone with 100 μg siRNA targeting the GAPDH gene. Seventy-two hours post administration the mice are sacrificed and brain, muscle, lung, kidney, and liver tissues are isolated from each animal. Tissues are split into two halves: one stored in RNAlater® (Ambion Incorporated, Austin, Tex.) and frozen in liquid N2; the other one is homogenized in disruption buffer. Tissue stored in RNAlater® is used for total RNA isolation (PARIS™ kit; Ambion Incorporated) and tissue homogenized in disruption buffer used for protein isolation.

Brain, muscle, lung, kidney, and liver tissues are isolated from the mice, and protein and total RNA is isolated from the tissues. Immunohistochemistry (RLIP76) is performed for 1 mouse from each group on brain and liver tissues. Real time qRT-PCR-based analysis is performed to determine GAPDH siRNA accumulation in tissues (5 tissues×9 animals=45 samples; duplicates: 90 samples total), and reduction of GAPDH mRNA expression in tissues (5 tissues×9 animals=45 samples; duplicates: 90 samples total).

Example 5

A study is conducted in a mouse model for the ability of RLIP liposomes to deliver a nucleic acid cargo molecule to various tissues when administered orally. The nucleic acid is an siRNA molecule to the GAPDH gene. Expression in the tissues is detected by RT-PCR and Western blot in samples 24 and 72 hours post administration.

Three groups of 3 wild-type balb/c mice are orally administered a single dose. Group 1 mice each receive 50 μg of RLIP76 proteoliposome with 100 μg siRNA targeting the GAPDH gene. Group 2 mice each receive 50 μg of RLIP76 proteoliposome with 100 μg negative control siRNA (scrambled sequence). Group 3 mice each receive liposomes alone with 100 μg siRNA targeting the GAPDH gene. Seventy-two hours post administration the mice are sacrificed and brain, muscle, lung, kidney, and liver tissues are isolated from each animal. Tissues are split into two halves: one stored in RNAlater® (Ambion Incorporated, Austin, Tex.) and frozen in liquid N2; the other one is homogenized in disruption buffer. Tissue stored in RNAlater® is used for total RNA isolation (PARIS™ kit; Ambion Incorporated) and tissue homogenized in disruption buffer used for protein isolation.

Brain, muscle, lung, kidney, and liver tissues are isolated from the mice, and protein and total RNA is isolated from the tissues. Immunohistochemistry (RLIP76) is performed for 1 mouse from each group on brain and liver tissues. Real time qRT-PCR-based analysis is performed to determine GAPDH siRNA accumulation in tissues (5 tissues×9 animals=45 samples; duplicates: 90 samples total), and reduction of GAPDH mRNA expression in tissues (5 tissues×9 animals=45 samples; duplicates: 90 samples total).

Example 6

A study is conducted in a mouse model for the ability of RLIP liposomes to deliver a nucleic acid cargo molecule to tumor tissue when administered by i.p. injection. The nucleic acid is a siRNA molecule to the Polo-like kinase 1 gene (Plk1 gene), which is essential for tumor cell mitosis and maintenance of genomic stability. Expression in the tissues is detected by RT-PCR and Western blot in samples 24 and 72 hours post administration. Functional effects of delivery are also measured by monitoring the size and growth of the targeted tumors after treatment.

LNCaP cells are derived from a human prostate cancer and frequently used for xenograft studies. For the study, 1 to 2×10$^6$ LNCaP cells are co-inoculated with 100 ml of Matrigel (BD Biosciences, Palo Alto, Calif.) into the right flank of immunocompromised NOD/SCID mice (mice are obtained from the NCI). The animals are examined twice weekly for the development of palpable tumors at the site of injection. When tumor volumes reach approximately 150-200 mm$^3$, tumor-bearing mice are randomly assigned to one of three groups (3 mice/group). Group 1 mice each receive 50 μg of RLIP76 proteoliposome with 100 μg siRNA targeting the Plk1 gene. Group 2 mice each receive 50 μg of RLIP76 proteoliposome with 100 μg negative control siRNA (scrambled sequence). Group 3 mice each receive liposomes alone with 100 siRNA targeting the Plk1 gene. Seventy-two hours post administration the mice are sacrificed and tumor, brain, muscle, lung, kidney, and liver tissues are isolated from each animal. Tissues are split into two halves: one stored in RNAlater® (Ambion Incorporated, Austin, Tex.) and frozen in liquid nitrogen; the other one is homogenized in disruption buffer. Tissue stored in RNAlater® is used for total RNA isolation (PARIS™ kit; Ambion Incorporated) and tissue homogenized in disruption buffer is used for protein isolation.

Tumor, brain, muscle, lung, kidney, and liver tissues are isolated from the mice, and protein and total RNA is isolated from the tissues. Immunohistochemistry (RLIP76) is performed for 1 mouse from each group on brain and liver tissues. Real time qRT-PCR-based analysis is performed to determine Plk1 siRNA accumulation in tissues.

The results of these studies will demonstrate delivery of Plk1 siRNA to tumor tissue compared to normal tissues.

For the next study, 1 to 2×10$^6$ LNCaP cells are co-inoculated with 100 ml of Matrigel (BD Biosciences, Palo Alto, Calif.) into the right flank of immunocompromised NOD/SCID mice (mice are obtained from the NCI). The animals are examined twice weekly for the development of palpable tumors at the site of injection. When tumor volumes reach approximately 150-200 mm$^3$, tumor-bearing mice are randomly assigned to one of three groups (3 mice/group). Group 4 mice each receive 50 μg of RLIP76 proteoliposome with 100 μg siRNA targeting the Polo-like kinase 1 gene (Plk1 gene), essential for tumor cell mitosis and maintenance of genomic stability. Group 5 mice each receive 50 μg of RLIP76 proteoliposome with 100 μg negative control siRNA (scrambled sequence). Group 6 mice each receive liposomes alone with 100 μg siRNA targeting the Plk1 gene. Tumor volumes are measured weekly and calculated by the formula: Volume=0.523× long diameter (mm)$^2$× short diameter (mm). Data points are reported as mean value±SD.

The results of these studies will demonstrate the effect of delivery of Plk1 siRNA to tumor tissue using RLIP76 proteoliposomes compared to delivery of a control siRNA to tumor tissue using RLIP76 proteoliposomes, and delivery of Plk1 siRNA to tumor tissue using control liposomes.

The above studies are repeated using oral administration to determine the ability of RLIP liposomes to deliver a nucleic acid cargo molecule to tumor tissue when administered orally.

The above studies, both with i.p. and oral administration, are repeated using A549 cells, which are a non-small cell lung cancer line that is often used for testing, to demonstrate delivery of Plk1 siRNA to tumor tissue compared to normal tissues, and demonstrate the effect of delivery of Plk1 siRNA to tumor tissue using RLIP76 proteoliposomes compared to delivery of a control siRNA to tumor tissue using RLIP76 proteoliposomes, and delivery of Plk1 siRNA to tumor tissue using control liposomes.

Example 7

A study is conducted in a mouse model for the ability of RLIP liposomes to deliver a nucleic acid cargo molecule to tumor tissue located in the brain when administered by i.p. injection. The nucleic acid is a siRNA molecule to the STAT3 gene, which is known to be abnormally active in D54-MG cells, a well-characterized human glioblastoma cell line, and necessary for their proliferation. Expression in the tissues is detected by RT-PCR and Western blot in samples 24 and 72 hours post administration. Functional effects of delivery are also measured by monitoring the size and growth of the targeted tumors after treatment.

In this study, s.c. xenografts passed in athymic mice are excised, minced, and disassociated with 0.5% collagenase at room temperature in a trypsinization flask for 2 hours. Viable cells are separated on a Ficoll density gradient, are washed twice with DPBS, resuspended in 2.5% methylcellulose at a concentration of 13×10$^7$ cells/ml, and are injected into an guide cannula implanted in the forebrain of BALBc mice through a 33-gauge infusion cannula in a volume of 10 μl using a 500-microliter Hamilton gas-tight syringe and injector (Hamilton Co., Reno, Nev.). On histological examination, tumors are consistently evident microscopically three days after tumor challenge and macroscopically evident at gross autopsy nine days after challenge. These macroscopic tumors are comparable in size, by volume extrapolation, to human gliomas of 4 cm in diameter. Mice are studied in groups of 5 according to the following schema.

Group 1 mice each receive 50 μg of RLIP76 proteoliposome with 100 μg siRNA targeting the STAT3 gene. Group 2 mice each receive 50 μg of RLIP76 proteoliposome with 100 μg negative control siRNA (scrambled sequence). Group 3 mice each receive liposomes alone with 100 μg siRNA targeting the STAT3 gene. Seventy-two hours post administration the mice are sacrificed and tumor, brain, muscle, lung, kidney, and liver tissues are isolated from each animal. Tissues are split into two halves: one stored in RNAlater® (Ambion Incorporated, Austin, Tex.) and frozen in liquid nitrogen; the other one is homogenized in disruption buffer. Tissue stored in RNAlater® is used for total RNA isolation (PARIS™ kit; Ambion Incorporated) and tissue homogenized in disruption buffer is used for protein isolation.

Tumor, brain, muscle, lung, kidney, and liver tissues are isolated from the mice, and protein and total RNA is isolated from the tissues. Immunohistochemistry (RLIP76) is performed for 1 mouse from each group on brain and liver tissues. Real time qRT-PCR-based analysis is performed to determine STAT3 siRNA accumulation in tissues.

The results of these studies will demonstrate delivery of STAT3 siRNA to tumor tissue compared to normal tissues.

In the next study, s.c. xenografts passed in athymic mice are excised, minced, and disassociated with 0.5% collagenase at room temperature in a trypsinization flask for 2 hours. Viable cells are separated on a Ficoll density gradient, are washed twice with DPBS, resuspended in 2.5% methylcellulose at a concentration of $13 \times 10^7$ cells/ml, and are injected into an guide cannula implanted in the forebrain of BALBc mice through a 33-gauge infusion cannula in a volume of 10 μl using a 500-microliter Hamilton gas-tight syringe and injector (Hamilton Co., Reno, Nev.). On histological examination, tumors are consistently evident microscopically three days after tumor challenge and macroscopically evident at gross autopsy nine days after challenge. These macroscopic tumors are comparable in size, by volume extrapolation, to human gliomas of 4 cm in diameter. Mice are studied in groups of 5 according to the following schema.

Group 4 mice each receive 50 μg of RLIP76 proteoliposome with 100 μg siRNA targeting the STAT3 gene. Group 5 mice each receive 50 μg of RLIP76 proteoliposome with 100 μg negative control siRNA (scrambled sequence). Group 6 mice each receive liposomes alone with 100 μg siRNA targeting the STAT3 gene. After 10 days, the mice are sacrificed and tumor measurements taken at gross autopsy, and tumor tissue is obtained for immunohistochemistry analysis with antibodies to Ki-67 and Annexin V to measure cell proliferation and apoptosis, respectively.

The above studies are repeated using oral administration to determine the ability of RLIP liposomes to deliver a nucleic acid cargo molecule to tumor tissue located in the brain when administered orally.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of delivering an RNA molecule to a subject comprising orally administering to the subject a composition comprising a proteoliposome comprising RLIP76 and the RNA molecule, wherein the RNA molecule is selected from the group consisting of an antisense RNA molecule, a small inhibitory RNA molecule, a short hairpin RNA molecule, a ribozyme, and a microRNA molecule.

2. The method of claim 1, wherein the RNA molecule is a small inhibitory RNA molecule.

3. The method of claim 1, wherein the RNA molecule is a microRNA molecule.

4. The method of claim 1, wherein the RNA molecule is not delivered to the brain.

5. The method of claim 1, wherein the RNA molecule is delivered to a tumor.

6. The method of claim 1, wherein 0.1 mg/kg to 10 mg/kg of the composition is administered to the subject.

7. The method of claim 1, wherein the composition further comprises a cell-specific targeting moiety.

8. The method of claim 6, wherein the cell is not a brain cell.

9. The method of claim 1, wherein the proteoliposomes are large vesicles.

10. The method of claim 1, wherein the RNA molecule is present in a therapeutically effective amount.

11. The method of claim 1, wherein the RNA molecule inhibits expression of SET-1.

12. The method of claim 1, wherein the RNA molecule inhibits expression of Plk1.

13. The method of claim 1, wherein the RNA molecule inhibits expression of STAT3.

* * * * *